United States Patent
Zhang et al.

(10) Patent No.: US 10,829,491 B2
(45) Date of Patent: Nov. 10, 2020

(54) PYRIMIDO[5,4-B]INDOLIZINE OR PYRIMIDO[5,4-B]PYRROLIZINE COMPOUND, PREPARATION METHOD AND USE THEREOF

(71) Applicant: SHANGHAI INSTITUTE OF MATERIA MEDICA, CHINESE ACADEMY OF SCIENCES, Shanghai (CN)

(72) Inventors: Ao Zhang, Shanghai (CN); Jian Ding, Shanghai (CN); Hua Xie, Shanghai (CN); Zilan Song, Shanghai (CN); Yu Xue, Shanghai (CN); Linjiang Tong, Shanghai (CN); Meiyu Geng, Shanghai (CN)

(73) Assignee: SHANGHAI INSTITUTE OF MATERIA MEDICA, CHINESE ACAD, Shanghai (CN)

( * ) Notice: Subject to any disclaimer, the term of this patent is extended or adjusted under 35 U.S.C. 154(b) by 0 days.

(21) Appl. No.: 16/463,868

(22) PCT Filed: Nov. 24, 2017

(86) PCT No.: PCT/CN2017/112729
§ 371 (c)(1),
(2) Date: May 24, 2019

(87) PCT Pub. No.: WO2018/095398
PCT Pub. Date: May 31, 2018

(65) Prior Publication Data
US 2019/0292183 A1    Sep. 26, 2019

(30) Foreign Application Priority Data

Nov. 24, 2016  (CN) .......................... 2016 1 1045301

(51) Int. Cl.
| | | |
|---|---|---|
| C07D 471/14 | (2006.01) | |
| A61P 35/00 | (2006.01) | |
| C07D 487/14 | (2006.01) | |
| A61K 31/519 | (2006.01) | |
| A61P 37/02 | (2006.01) | |
| A61P 35/02 | (2006.01) | |
| A61P 29/00 | (2006.01) | |

(52) U.S. Cl.
CPC .......... C07D 471/14 (2013.01); A61K 31/519 (2013.01); A61P 29/00 (2018.01); A61P 35/00 (2018.01); A61P 35/02 (2018.01); A61P 37/02 (2018.01); C07D 487/14 (2013.01)

(58) Field of Classification Search
CPC .................................................. C07D 471/14
See application file for complete search history.

(56) References Cited

FOREIGN PATENT DOCUMENTS

| CN | 104136438 A | 11/2014 |
|---|---|---|
| CN | 105073752 A | 11/2015 |

OTHER PUBLICATIONS

McMahon et al. (2000).*
Pindedo et al. (2000).*
Rixson, James E. et al. The Development of Domino Reactions Incorporating the Heck Reaction: The Formation of N-Heterocycles. European Journal of Organic Chemistry. Nov. 30, 2011 (Nov. 30, 2011), 2012(3), pp. 544 to 558.
Huang, Qinhua et al. Synthesis of Cyclopropanes by Pd-catalyzed Activation of Alkyl C-H Bonds. Tetrahedron Letters. Oct. 8, 2009 (Oct. 8, 2009), 50(52), pp. 7235 to 7238.
International Search Report issued in corresponding PCT Application No. PCT/CN2017/112729 dated Mar. 7, 2018.

* cited by examiner

*Primary Examiner* — Paul V Ward
(74) *Attorney, Agent, or Firm* — Carter, DeLuca & Farrell LLP

(57) ABSTRACT

The present disclosure relates to a Pyrimido[5,4-b]indolizine or pyrimido[5,4-b]pyrrolizine compound, preparation method thereof and use thereof. The compounds of the present invention have good inhibitory activities against BTK at the molecular and cellular levels. Importantly, the compounds of the present invention have low activity against Ramos cells of normal human B lymphoma cells, and have high activity against BTK-sensitive human diffuse large B lymphoma TMD8 cells, indicating that these type of compounds with novel structural are highly selective, off-target phenomenon and corresponding side effects are low. Thus it is a selective inhibitor of BTK with development potential.

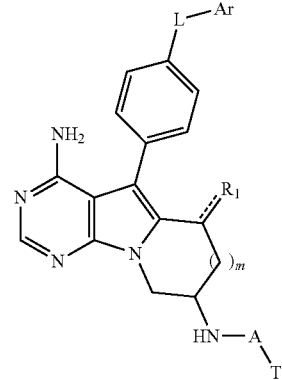

Formula I

8 Claims, No Drawings

PYRIMIDO[5,4-B]INDOLIZINE OR PYRIMIDO[5,4-B]PYRROLIZINE COMPOUND, PREPARATION METHOD AND USE THEREOF

CROSS REFERENCE TO RELATED APPLICATIONS

This application is a national stage application of International Application No. PCT/CN2017/112729, filed Nov. 24, 2017, which claims the benefit of and priority to Chinese Patent Application No. 201611045301.1, filed Nov. 24, 2016, the entire contents of each of which are hereby incorporated by reference herein in their entirety.

TECHNICAL FIELD

The present disclosure relates to small molecule inhibitors targeting BTK kinase, and in particular to a pyrimido[5,4-b]indolizine or pyrimido[5,4-b]pyrrolizine compound, preparation method and use thereof.

BACKGROUND ART

Bruton's tyrosine kinase (BTK) is a class of non-receptor tyrosine kinases, and belongs to the TEC tyrosine kinase family including Tec, Bmx, BTK, Itk and Txk. BTK is currently a clinically proven drug target in the TEC family.

BTK is mainly expressed in cells related to hematopoietic system, such as B cells, mast cells, macrophages, and the like. B cells produce a variety of physiological signals through signal transduction of the B cell receptor (BCR). BCR signaling pathway plays a key role in the development and mutation of B cells. BCR signaling pathway disorder and dysfunction often lead to severe immunodeficiency and inflammatory response, and BCR signaling pathway is also closely related to the occurrence and development of a variety of B cell-associated tumors. BTK is a key regulator in the formation of early B cells and survival of mature B cells, and mediates upstream signaling pathway of BCR signaling pathway. In addition, BTK is also closely related to cell proliferation and apoptosis. After stimulating the body's immune response, BCR recognizes the antigen, and activates the expression of NF-κB/Rel transcription factors by BTK-mediated BCR signaling pathway to regulate the proliferation of B cells. On the other hand, the activated BTK can also regulate the transcriptional activity of BAP-135/TFII-I, and then regulate the expression of apoptosis-related proteins such as VpreB, CD5 and Bcl-2. Therefore, inhibitors against BTK can be used to treat certain hematological tumor and autoimmune diseases.

Ibrutinib developed by Pharmacyclics Inc. is the only commercially available small molecule inhibitor targeting BTK kinase currently. The drug is approved to the market in November 2013 by FDA, as a breakthrough therapeutic drug for clinical treatment of relapsed or refractory mantle cell lymphoma (MCL). Ibrutinib has an overall relief rate of 65.8%, with a median duration of relief of 1.9 months. However, ibrutinib has a relatively severe toxic and side effect, since it has a good inhibition for kinase such as Tek and EGFR.

Therefore, there is still a need to further develop other small molecule inhibitors targeting BTK kinase.

SUMMARY OF THE INVENTION

The present disclosure provides a 5-aryl-pyrimidoindolizine or 5-aryl-pyrimidopyrrolizine compound as shown in formula I or a pharmaceutically acceptable salt thereof,

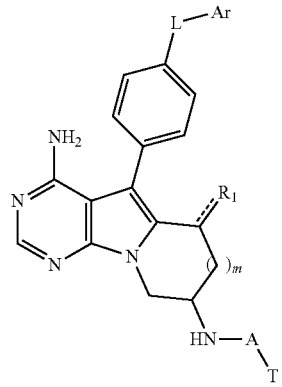

Formula I wherein:
$R_1$ is H, methyl or methylidene;
L is —O—, —C(=O)NH— or —C(=O)NHCHR$_2$—, wherein, $R_2$ is hydrogen or substituted or unsubstituted C1-C3 alkyl, wherein, the substituent in $R_2$ is halogen or C1-C3 alkoxy;
m is 0 or 1;
Ar is substituted or unsubstituted C6-C20 aryl, substituted or unsubstituted 5-20 membered heteroaryl containing one or more heteroatoms selected from the group consisting of O, N and S, preferably substituted or unsubstituted C6-C10 aryl, substituted or unsubstituted 5-10 membered heteroaryl containing one or more heteroatoms selected from the group consisting of O, N and S, more preferably substituted or unsubstituted phenyl, substituted or unsubstituted 5 to 6-membered heteroaryl (particularly pyridyl), wherein the substituent in Ar is halogen, C1-C6 alkyl, C1-C6 alkoxy, trifluoromethyl or trifluoromethoxy, preferably halogen, C1-C3 alkyl, C1-C3 alkoxy, trifluoromethyl or trifluoromethoxy, more preferably halogen, C1-C3 alkyl, C1-C3 alkoxy, trifluoromethyl or trifluoromethoxy;
A is carbonyl, sulfonyl, or

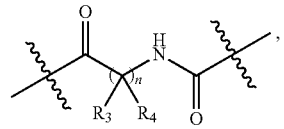

wherein $R_3$ and $R_4$ may be independently hydrogen or C1-C3 alkyl, or $R_3$, $R_4$ and the carbon atom attached thereto form C3-C5 cycloalkyl;
n is 0, 1 or 2, preferably 0 or 1;
T is

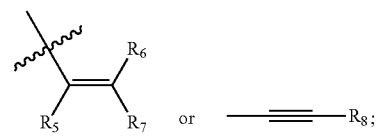

$R_5$, $R_6$ and $R_7$ may be independently selected from the group consisting of hydrogen, cyano, halogen, and substituted or unsubstituted C1-C20 alkyl, preferably are independently selected from the group consisting of hydrogen, cyano, halogen, and substituted or unsubstituted C1-C10 alkyl, more preferably are independently selected from the group consisting of hydrogen, cyano, halogen, and substituted or unsubstituted C1-C5 alkyl; the substituent in $R_5$, $R_6$ or $R_7$ is dimethylamino, C1-C10 alkoxy, or 3 to 10 membered heterocyclyl containing one or more heteroatoms selected from the group consisting of O, N and S; preferably dimethylamino, C1-C6 alkoxy, or 3 to 10 membered heterocyclyl containing one or more heteroatoms selected from the group consisting of O, N and S; more preferably dimethylamino, C1-C5 alkoxy, or 3 to 6 membered heterocyclyl containing 1 to 3 heteroatoms selected from the group consisting of O, N and S;

$R_8$ is selected from the group consisting of hydrogen and C1-C10 alkyl, preferably selected from the group consisting of hydrogen and C1-C5 alkyl, more preferably selected from the group consisting of hydrogen and C1-C3 alkyl.

In one embodiment, L is —O— or —C(=O)NH—.

In one embodiment, Ar is phenyl, 4-fluorophenyl, 4-trifluoromethylphenyl, pyridin-2-yl, 3-fluoropyridin-6-yl or 4-trifluoromethylpyridine-6-yl.

In one embodiment, $R_3$ is hydrogen.

In one embodiment, $R_4$ is H or methyl.

In one embodiment, $R_3$, $R_4$ and the carbon atom attached thereto form cyclopropyl.

In one embodiment, n is 0.

In one embodiment, $R_5$ is H, cyano or methyl.

In one embodiment, $R_6$ is H.

In one embodiment, $R_7$ is H, t-butyl or dimethylaminomethyl.

In one embodiment, $R_8$ is H or methyl.

In one embodiment, T is vinyl or propynyl.

In the present invention, halogen includes fluorine, chlorine, bromine and iodine.

In the present invention, C6-C20 aryl means a 6-20 membered monocyclic or polycyclic aromatic group whose ring is composed of only carbon atoms, such as phenyl, naphthyl or the like. C6-C10 aryl has a similar meaning.

In the present invention, 5-20 membered heteroaryl means a 5-20 membered monocyclic or polycyclic aromatic group whose ring comprises one or more heteroatoms selected from the group consisting of O, N and S, e.g., furanyl, pyrrolyl, pyridyl, pyrimidinyl and the like. 5-10 and 5-6 membered heteroaryl have a similar meaning.

In the present invention, 3 to 10 membered heterocyclyl means a 3-10 membered monocyclic or polycyclic non-aromatic group whose ring comprises one or more heteroatoms selected from the group consisting of O, N and S, e.g., aziridinyl, oxiranyl, azetidinyl, oxetanyl, tetrahydrofuranyl, azacyclopentanyl, piperidinyl and the like. 3-6 membered heterocyclyl has a similar meaning.

More preferably, the compound is selected from the group consisting of the compounds shown in the following table:

| Compound | Structure |
|---|---|
| S1 | 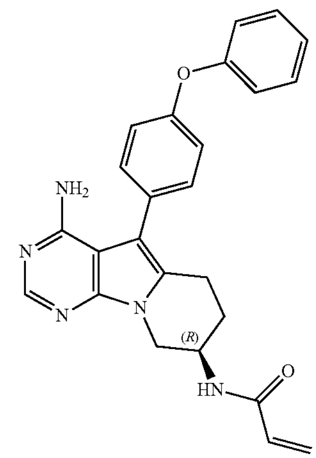 |
| S2 | 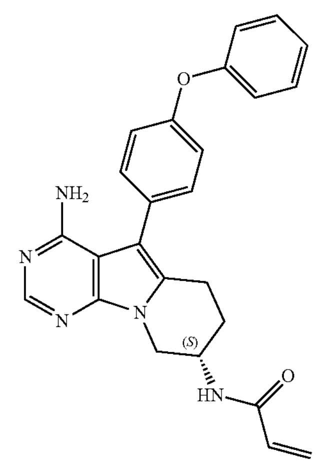 |
| S3 | 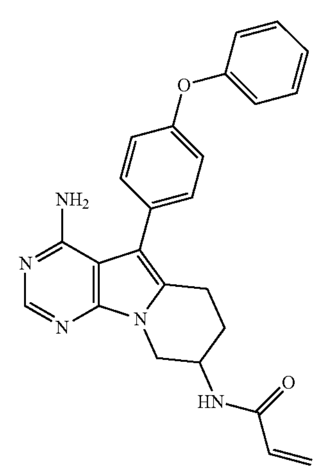 [SMILES: C=CC(=O)NC1CCc2c(-c3ccc(Oc4ccccc4)cc3)c3c(N)ncnc3n2C1] |

| Compound | Structure |
|---|---|
| S4 | 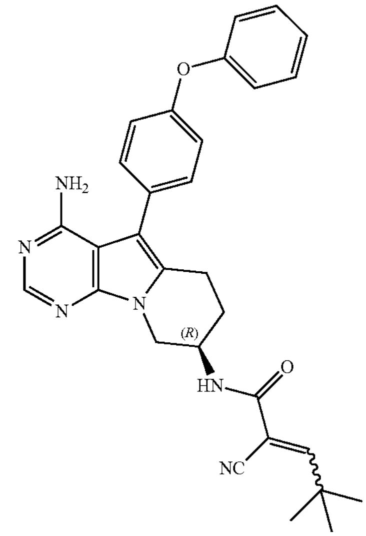 |
| S5 | 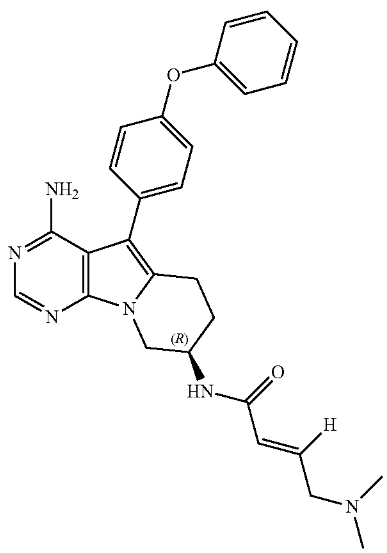 |
| S6 | 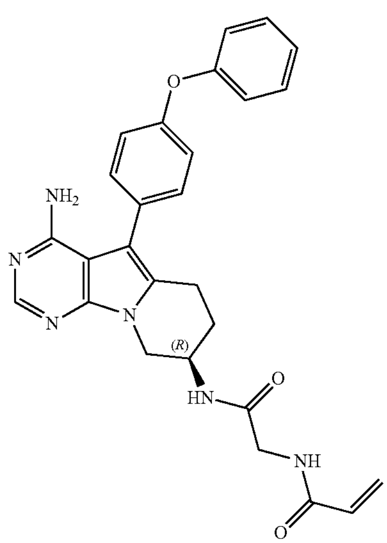 |
| S7 | |
| S8 | |
| S9 | |

| Compound | Structure |
|---|---|
| S10 | 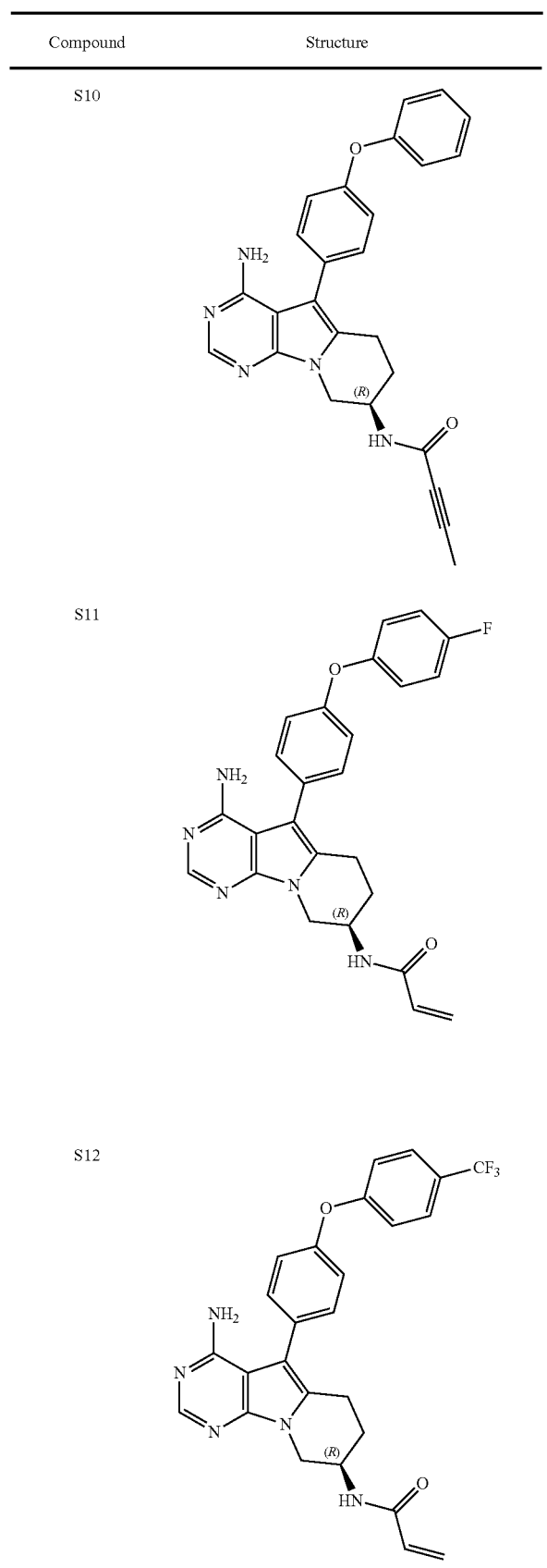 |
| S11 | |
| S12 | |
| Compound | Structure |
|---|---|
| S13 | 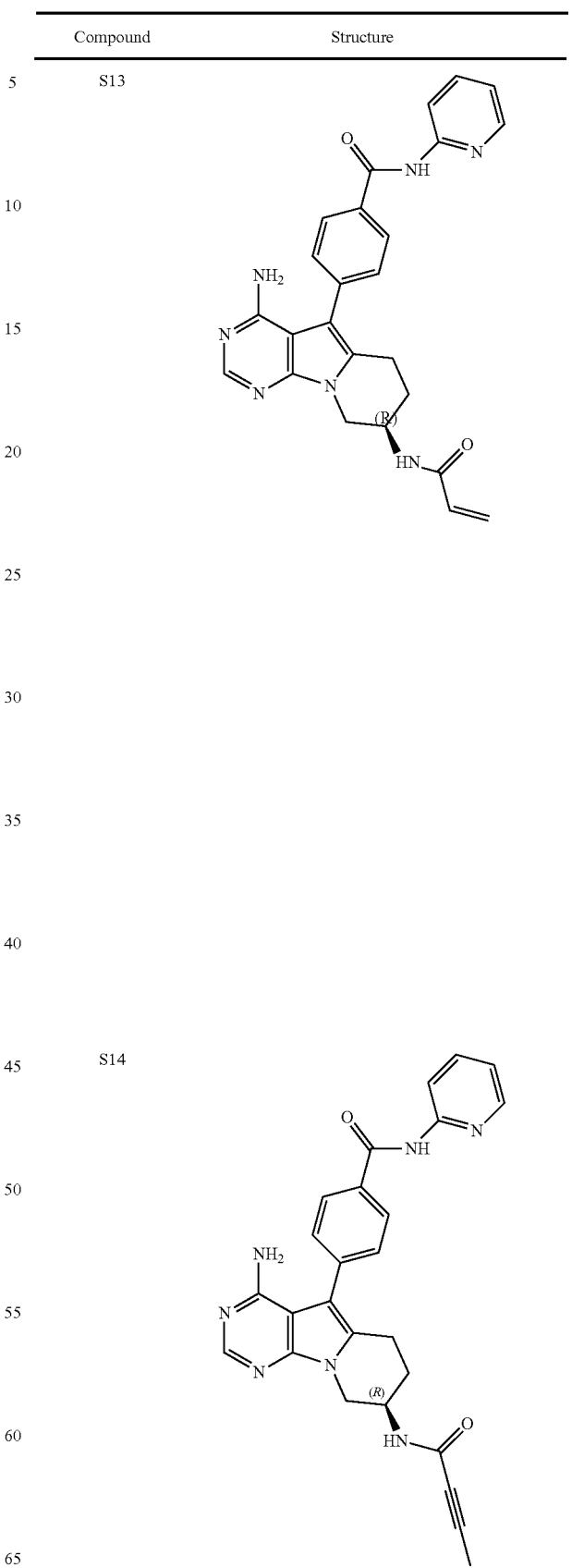 |
| S14 | |

| Compound | Structure |
|---|---|
| S15 | 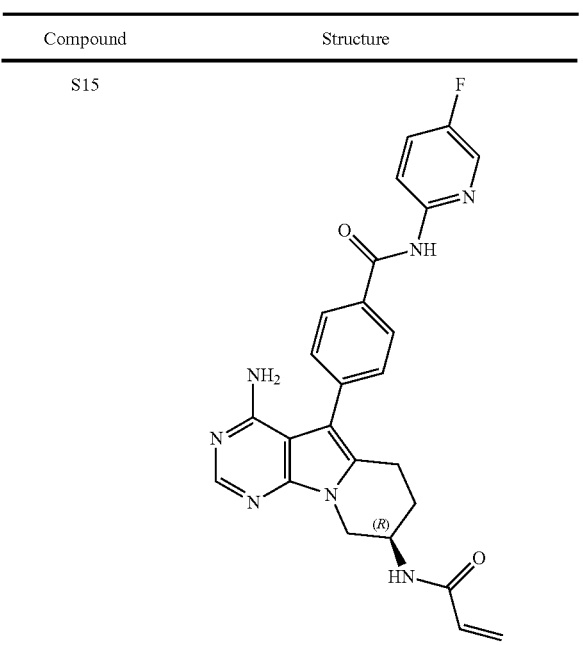 |
| S16 | 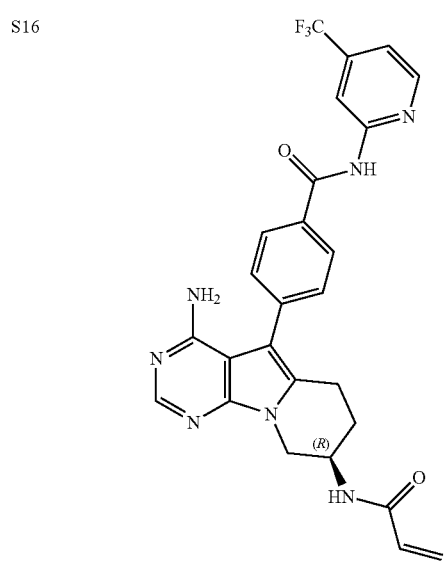 |
| S17 | 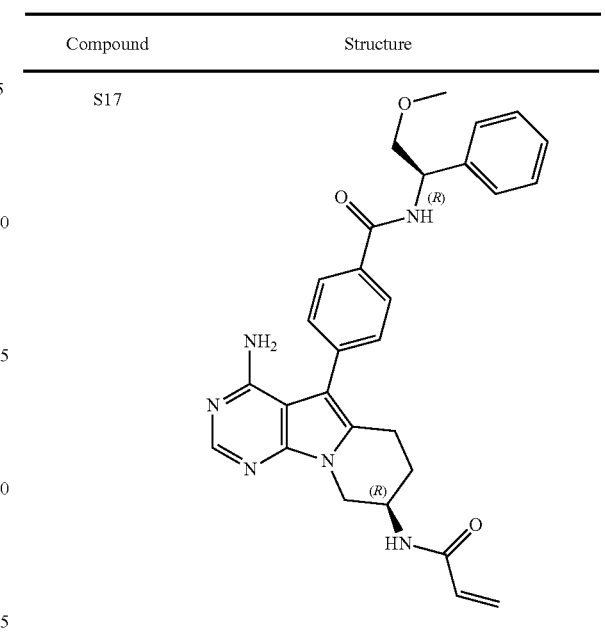 |
| S18 | 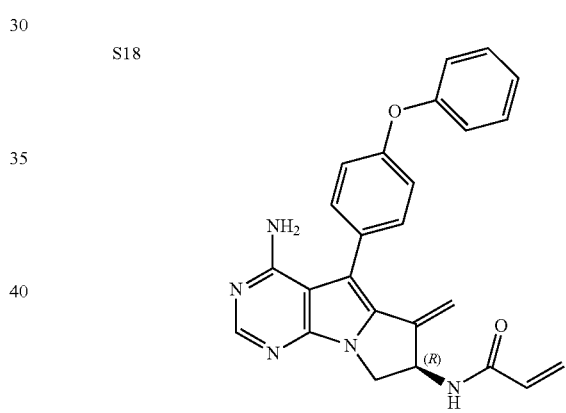 |
| S19 | 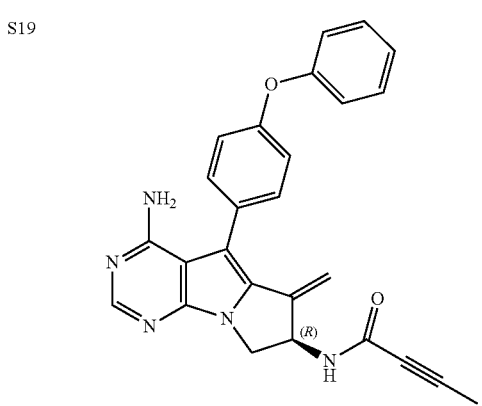 |

| Compound | Structure |
|---|---|
| S20 | (structure) |
| S21 | (structure) |

| Compound | Structure |
|---|---|
| S22 | (structure) |

The present invention also provides a method for preparing 5-aryl-pyrimidoindolizine or 5-aryl-pyrimidopyrrolizine compound. The abbreviations and symbols used in the preparation method (also in the other locations of the present description) are as follows:

Abbreviations and Symbols

9-BBN: 9-boronbicyclo[3.3.1]nonane
DCM: dichloromethane
DIAD: diisopropyl azodicarboxylate
DIPEA: diisopropylethylamine
DMF: N,N-dimethylformamide
EA: ethyl acetate
HATU: 2-(7-oxybenzotriazole)-N,N,N',N'-tetramethylurea hexafluorophosphate
NBS: N-bromosuccinimide
NIS: N-iodosuccinimide
PdCl$_2$(dppf): [1,1'-bis(diphenylphosphinyl)ferrocene]palladium dichloride
PE: petroleum ether
THF: tetrahydrofuran The preparation method of the compound includes the following steps:

Scheme 1

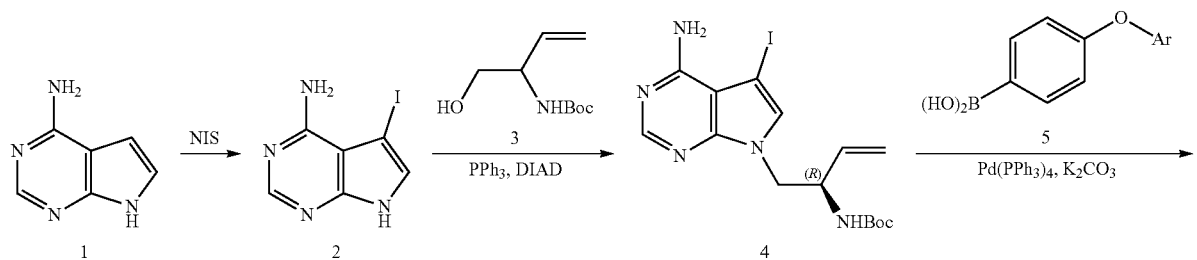

-continued
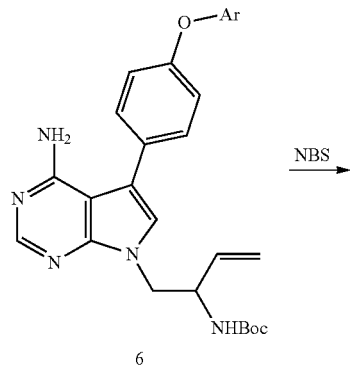
6
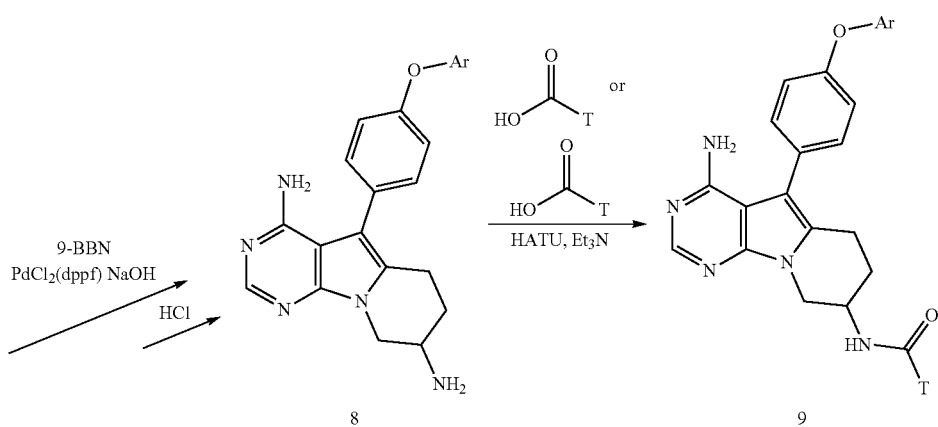
7 8 9
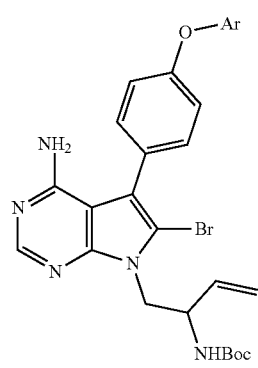
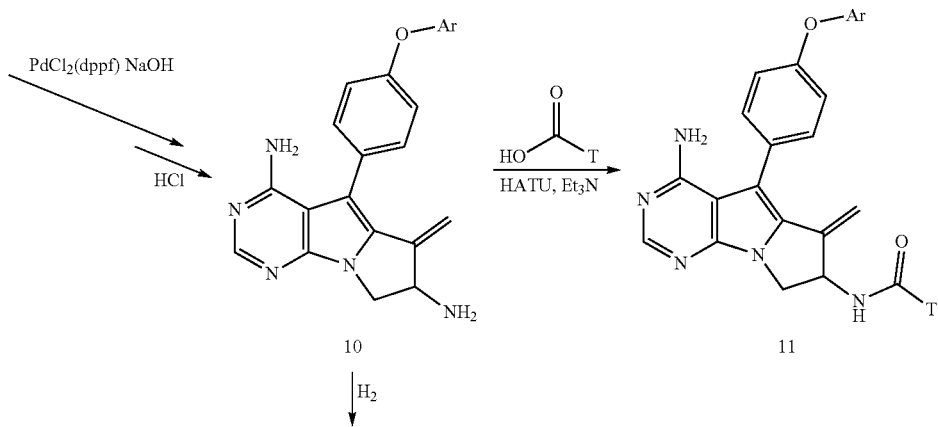
10 11

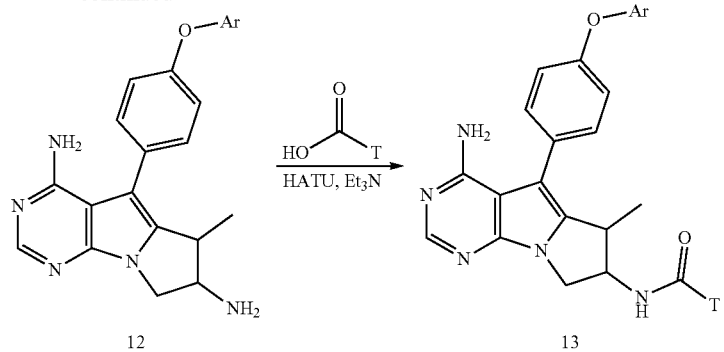

Scheme 1a:

Commercially available 4-amino-pyrrolo[2,3-d]pyrimidine, i.e. Compound 1 as a starting material is iodo-substituted with N-iodosuccinimide (NIS) on 5-position to give Compound 2, Fragment 3 is incorporated into Compound 2 through Mitsunobu reaction to give compound 4, Compound 4 is coupled with a substituted phenylboronic acid or borate to give Compound 6, Bromine is introduced at 6-position of Compound 6 by N-bromosuccinimide (NBS) to give Compound 7, Compound 7 reacts with 9-boronbicyclo[3.3.1]nonane (9-BBN) in anhydrous tetrahydrofuran (THF), then forms a six-membered ring through a self-Suzuki-Miyaura coupling in the presence of [1,1'-bis(diphenylphosphinyl)ferrocene] palladium dichloride ($PdCl_2$(dppf)), and is deprotected to give Compound 8 with a core of tetrahydrogenpyrido[5,4-b]indole, Compound 8 condensates with a carboxylic acid or a sulfonic acid to give Compound 9, or Scheme 1b:

Compound 7 forms a five-membered cyclic compound through an intramolecular Heck reaction in the presence of $PdCl_2$(dppf), and is deprotected to give Compound 10, which condensates with a substituted carboxylic acid to give Compound 11, or Scheme 1c:

Compound 10 is hydrogenated in the presence of a catalyst to give Compound 12,

Compound 12 condensates with an acid to give Compound 13;

or

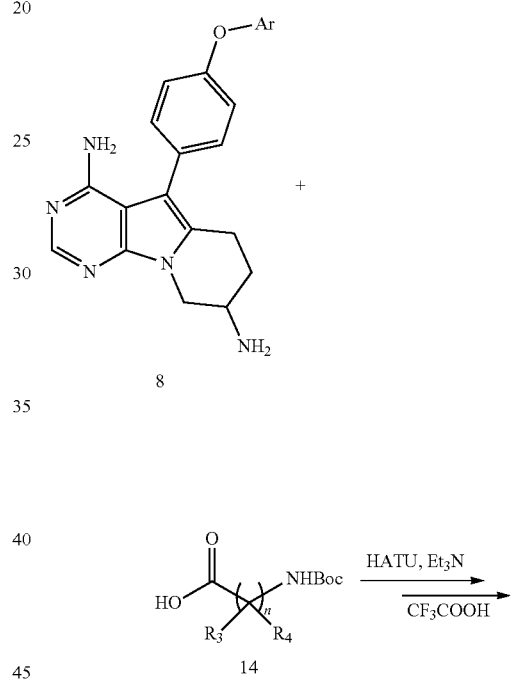

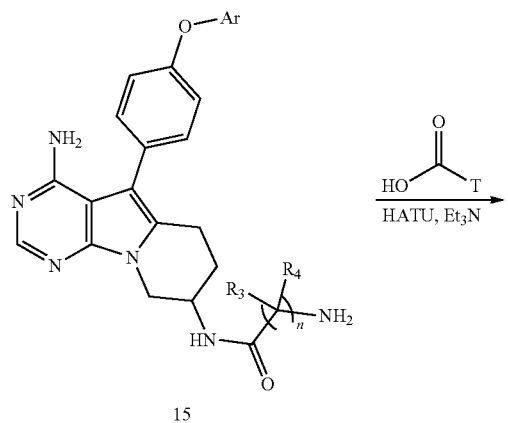

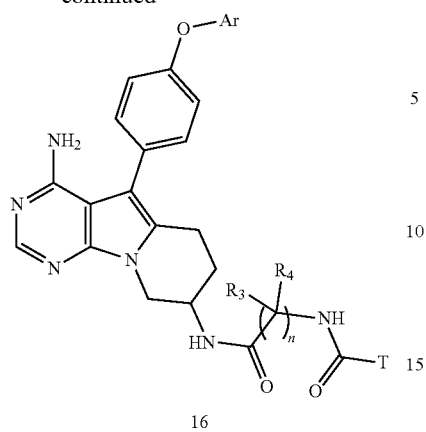
Compound 8 condensates with a N-Boc protected amino acid 14, and is deprotected to give Compound 15,
Compound 15 condensates with a substituted carboxylic acid to give Compound 16;
or
Scheme 3
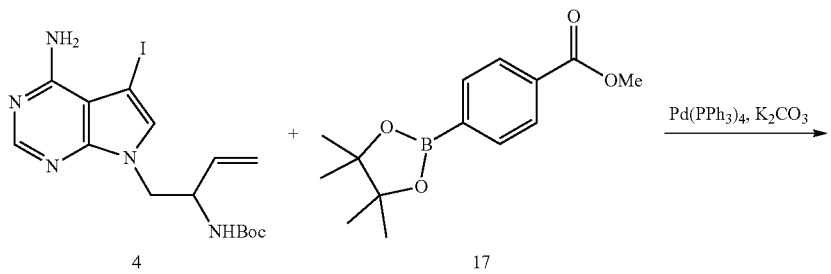
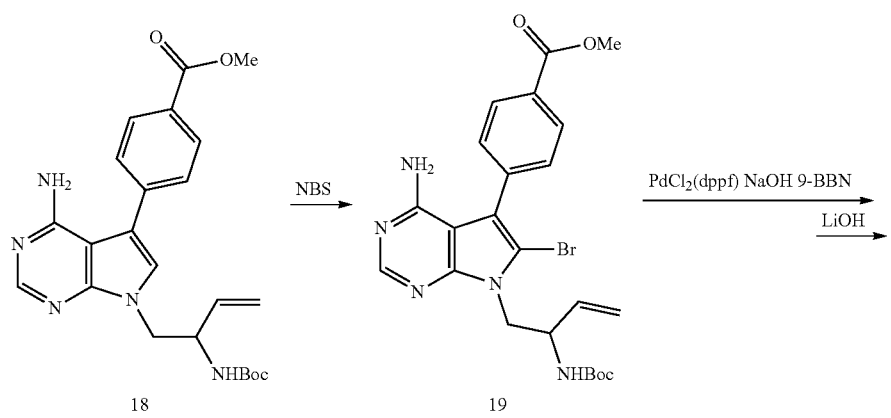

19

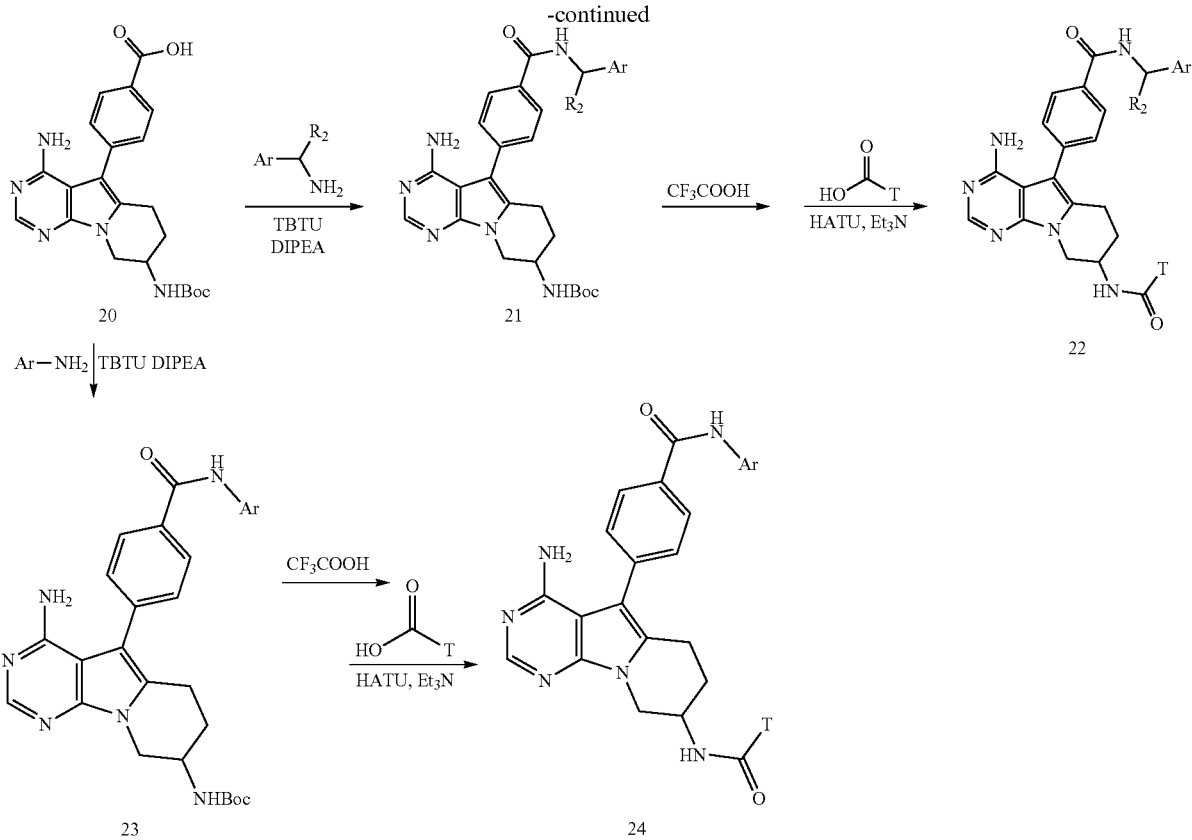

Scheme 3a:

Compound 4 is coupled with a substituted phenylboronic acid or borate 17 to give Compound 18, Bromine is incorporated at 6-position of Compound 18 by NBS to give brominated Compound 19, Compound 19 reacts with 9-BBN in anhydrous THF, forms a six-membered ring through a self-Suzuki-Miyaura coupling in the presence of PdCl$_2$(dppf), and then is hydrolyzed in the presence of lithium hydroxide to give Compound 20, Compound 20 condensates with a substituted alkylamine to give Compound 21, Compound 21 is deprotected and condensates with a carboxylic acid to give Compound 22, or Scheme 3b:

Compound 20 condensates with an arylamine to give Compound 23,

Compound 23 is deprotected and condensates with a carboxylic acid to give Compound 24;

or

20

Scheme 4

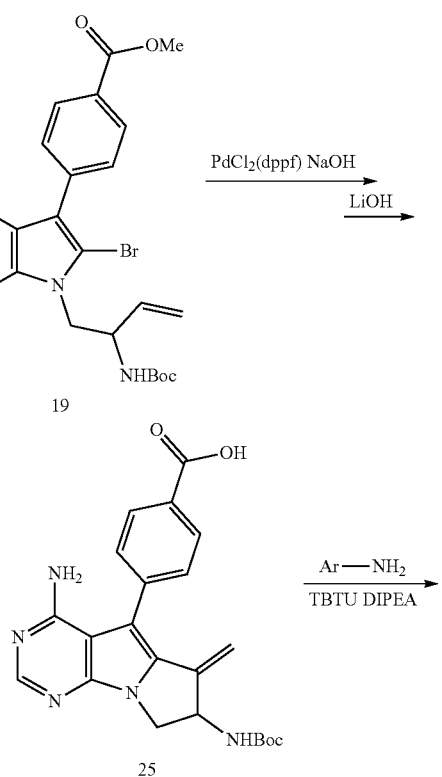

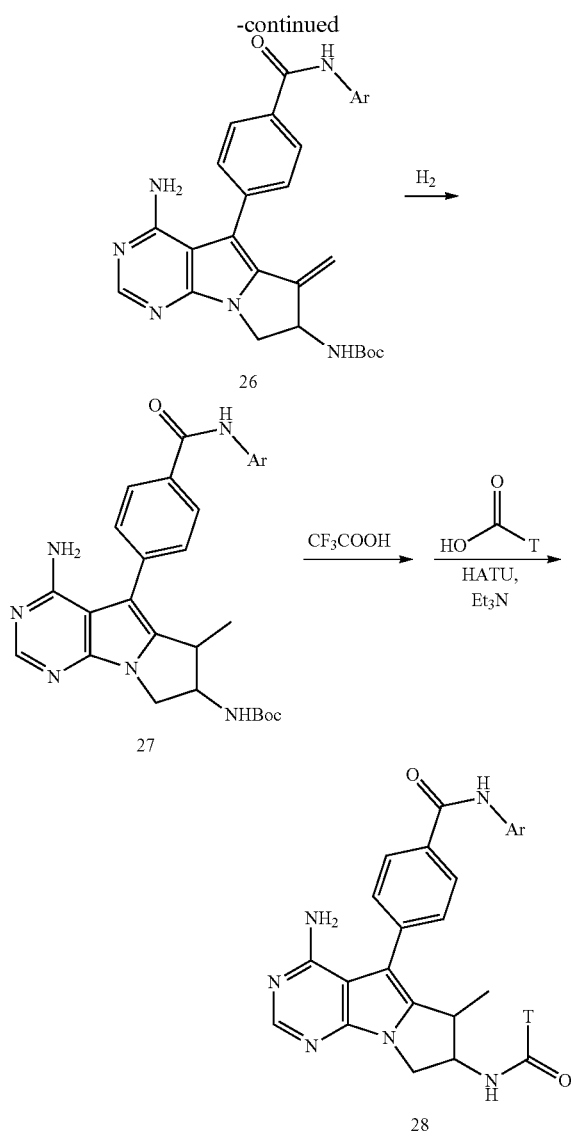

26

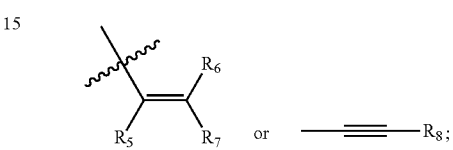

27

28

Brominated compound 19 forms a five-membered cyclic compound through an intramolecular Heck reaction in the presence of PdCl$_2$(dppf), and treated with LiOH to give a carboxylic acid 25, The carboxylic acid 25 condensates with an arylamine to give an amide 26, The amide 26 is hydrogenated in the presence of a catalyst to give Compound 27, Compound 27 is deprotected with CF$_3$COOH to remove Boc-protection, and condensates with a carboxylic acid to give Compound 28.

In the above reactions,

R$_2$ is hydrogen or substituted or unsubstituted C1-C3 alkyl, wherein the substituent in R$_2$ is halogen or C1-C3 alkoxy;

Ar is substituted or unsubstituted C6-C20 aryl, substituted or unsubstituted 5-20 membered heteroaryl containing one or more heteroatoms selected from the group consisting of O, N and S, preferably substituted or unsubstituted C6-C10 aryl, substituted or unsubstituted 5-10 membered heteroaryl containing one or more heteroatoms selected from the group consisting of O, N and S, more preferably substituted or unsubstituted phenyl, substituted or unsubstituted 5 to 6-membered heteroaryl (particularly pyridyl), wherein the substituent in Ar is halogen, C1-C6 alkyl, C1-C6 alkoxy, trifluoromethyl or trifluoromethoxy, preferably halogen, C1-C3 alkyl, C1-C3 alkoxy, trifluoromethyl or trifluoromethoxy, more preferably halogen, C1-C3 alkyl, C1-C3 alkoxy, trifluoromethyl or trifluoromethoxy;

R$_3$ and R$_4$ may be independently hydrogen or C1-C3 alkyl, or R$_3$, R$_4$ and the carbon atom attached thereto form C3-C5 cycloalkyl;

n is 0, 1 or 2, preferably 0 or 1;

T is $$\begin{array}{c} R_6 \\ \diagup \\ R_5 \diagdown R_7 \end{array} \quad \text{or} \quad \equiv\!\!\!-R_8;$$

R$_5$, R$_6$ and R$_7$ may be independently selected from the group consisting of hydrogen, cyano, halogen, and substituted or unsubstituted C1-C20 alkyl, preferably are independently selected from the group consisting of hydrogen, cyano, halogen, and substituted or unsubstituted C1-C10 alkyl, more preferably are independently selected from the group consisting of hydrogen, cyano, halogen, and substituted or unsubstituted C1-C5 alkyl; the substituent in R$_5$, R$_6$ or R$_7$ is dimethylamino, C1-C10 alkoxy, or 3 to 10 membered heterocyclyl containing one or more heteroatoms selected from the group consisting of O, N and S; preferably dimethylamino, C1-C6 alkoxy, or 3 to 10 membered heterocyclyl containing one or more heteroatoms selected from the group consisting of O, N and S; more preferably dimethylamino, C1-C5 alkoxy, or 3 to 6 membered heterocyclyl containing 1 to 3 heteroatoms selected from the group consisting of O, N and S;

R$_8$ is selected from the group consisting of hydrogen and C1-C10 alkyl, preferably selected from the group consisting of hydrogen and C1-C5 alkyl, more preferably selected from the group consisting of hydrogen and C1-C3 alkyl.

In one embodiment, Ar is phenyl, 4-fluorophenyl, 4-trifluoromethylphenyl, pyridin-2-yl, 3-fluoropyridin-6-yl or 4-trifluoromethylpyridine-6-yl.

In one embodiment, R$_3$ is hydrogen.

In one embodiment, R$_4$ is H or methyl.

In one embodiment, R$_3$, R$_4$ and the carbon atom attached thereto form cyclopropyl.

In one embodiment, n is 0.

In one embodiment, R$_5$ is H, cyano or methyl.

In one embodiment, R$_6$ is H.

In one embodiment, R$_7$ is H, t-butyl or dimethylaminomethyl.

In one embodiment, R$_8$ is H or methyl.

In one embodiment, T is vinyl or propynyl.

The compounds of the invention may have asymmetric centers, chiral axes and chiral planes, and may exist in the form of enantiomers, diastereomers, racemates, and mixtures thereof.

The pharmaceutically acceptable salt of the compound of formula I may be a conventional non-toxic salt formed by reaction of the compound of formula I with an inorganic or organic acid. For example, a conventional non-toxic salt may be prepared by reacting a compound of formula I with an inorganic or organic acid. The inorganic acid includes hydrochloric acid, hydrobromic acid, sulfuric acid, nitric acid, aminosulfonic acid, phosphoric acid, and the like. And the organic acid include citric acid, tartaric acid, lactic acid, pyruvic acid, acetic acid, benzenesulfonic acid, p-toluenesulfonic acid, methanesulfonic acid, naphthalenesulfonic acid, ethanesulfonic acid, naphthalenedisulfonic acid, maleic acid, malic acid, malonic acid, fumaric acid, succinic acid, propionic acid, oxalic acid, trifluoroacetic acid, stearic acid, pamoic acid, hydroxymaleic acid, phenylacetic acid, benzoic acid, salicylic acid, glutamic acid, ascorbic acid, p-aminobenzenesulfonic acid, 2-acetoxybenzoic acid, hydroxyethanesulfonic acid, etc. Alternatively, the pharmaceutically acceptable salt of the compound of formula I may be a sodium salt, a potassium salt, a calcium salt, an aluminum salt or an ammonium salt, which is formed by reacting the compound of formula I with propionic acid, oxalic acid, malonic acid, succinic acid, fumaric acid, maleic acid, lactic acid, malic acid, tartaric acid, citric acid, aspartic acid or glutamic acid to form an ester, and then reacting with an inorganic base; or a methylamine salt, ethylamine salt or ethanolamine salt formed by reacting a compound of the formula I with an organic base; or an inorganic acid salt which is formed by reacting the compound of formula I with lysine, arginine or ornithine to form an ester, and then reacting with hydrochloric acid, hydrobromic acid, hydrofluoric acid, sulfuric acid, nitric acid or phosphoric acid; or an organic acid salt which is formed by reacting the compound of formula I with lysine, arginine or ornithine to form an ester, and then reacting with formic acid, acetic acid, picric acid, methanesulfonic acid and ethanesulfonic acid.

The present invention provides use of a compound of the above formula I for manufacture of a medicament in treatment of a disease associated with the BTK kinase signal transduction pathway.

The invention also provides use of a compound of the above formula I in treatment of a disease associated with the BTK kinase signal transduction pathway.

The invention also provides a method of treating a disease associated with a BTK kinase signal transduction pathway, which comprises administering a therapeutically effective amount of one or more compounds of the above formula I or a pharmaceutically acceptable salt thereof to a subject.

The disease associated with the BTK kinase signal transduction pathway is selected from the group consisting of, for example, cancer, hyperplasia, restenosis, immune disorders, and inflammation.

The invention also provides use of a compound of the above formula I in manufacture of a medicament for inhibiting BTK kinase.

The invention also provides a pharmaceutical composition comprising a therapeutically effective amount of a compound of the above formula I or a pharmaceutically acceptable salt thereof, and one or more pharmaceutically acceptable carriers. The pharmaceutical composition may further comprise a pharmaceutical excipient such as an odorant, a fragrance, and the like.

The pharmaceutical composition of the present invention preferably contains an active ingredient in a weight ratio of 1 to 99%. Preferably, the compound of the formula I is in a ratio of 65% to 99% by weight as an active ingredient, and the remainder being pharmaceutically acceptable carriers, such as a diluent or a solvent or a salt solution.

The compounds and compositions of the invention are also useful in treatment, prevention or modulation of cancer cells and metastatic tumors of cancer. Accordingly, the present invention also provides use of a compound of the above formula I in manufacture of a medicament for treatment, prevention or modulation of cancer cells and metastatic tumors of cancer.

The cancer in the present invention includes, but is not limited to, histiocytic lymphoma, ovarian cancer, head and neck squamous cell carcinoma, gastric cancer, breast cancer, childhood hepatocellular carcinoma, colorectal cancer, cervical cancer, lung cancer, sarcoma, nasopharyngeal carcinoma, pancreatic cancer, glioblastoma, prostate cancer, small cell lung cancer, non-small cell lung cancer, multiple myeloma, thyroid cancer, testicular cancer, cervical cancer, endometrial cancer, esophageal cancer, leukemia, renal cell carcinoma, bladder cancer, liver cancer, astrocytoma, etc.; more preferably head and neck squamous cell carcinoma, histiocytic lymphoma, lung adenocarcinoma, small cell lung cancer, non-small cell lung cancer, pancreatic cancer, papillary kidney cells cancer, liver cancer, gastric cancer, colon cancer, multiple myeloma, and glioblastoma; preferably, the cancer is lymphoma.

The compound and the pharmaceutical composition of the present invention may be in various forms such as tablets, capsules, powders, syrups, solutions, suspensions, aerosols, and the like, and may be present in a suitable solid or liquid carrier or diluent, and a suitable sterilizing device for injection or drip.

Various dosage forms of the pharmaceutical composition of the present invention can be prepared according to a conventional preparation method in the pharmaceutical art. A unit dosage of the formulation contains 0.05 mg to 200 mg of the compound of formula I, preferably, a unit dosage of the formulation contains 0.1 mg to 100 mg of the compound of formula I.

The compound and the pharmaceutical composition of the present invention can be clinically administered to a mammal, including human and animal, and can be administered via a route such as oral, nose, skin, lung, or gastrointestinal tract, most preferably via oral. The most preferred daily dose is 0.01 to 200 mg/kg body weight by once, or 0.01 to 100 mg/kg body weight by several times. The optimal dosage for the individual should be based on the particular treatment regardless of the method of administration. Usually, the most suitable dose is determined by starting with a small dose, and then gradually increasing the dose until it is found.

According to the experiments of the present invention, the compound of the present invention has good inhibitory activities against BTK at molecular and cellular level. Importantly, the compound of the present invention has low activity against normal human B lymphoma Ramos cells, and high activity against BTK-sensitive human diffuse large B lymphoma TMD8 cells, indicating that this type of compounds with novel structure have a high selectivity, and low off-target possibility and low side effects, and thus are a class of selective inhibitor of BTK with development potential.

BEST MODE FOR CARRYING OUT THE INVENTION

Example 1: S1

(R)—N-(4-amino-5-(4-phenoxyphenyl)-6,7,8,9-tetrahydropyrimido[5,4-b]indolizin-8-yl)acrylamide (Scheme 1)

Step 1

Synthesis of 4-amino-5-iodo-7H-pyrrolo[2,3-d]pyrimidine

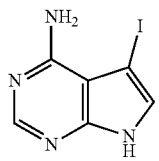

4-amino-7H-pyrrolo[2,3-d]pyrimidine (2.7 g, 20 mmol) was dissolved in 60 mL of chloroform, NIS (4.5 g, 20 mmol) was added therein. The reaction solution was refluxed for 2 h, and the insolubles were collected by filtration. The crude was purified by column chromatography with CHCl$_3$/MeOH=20/1 to give 4.2 g of target product, yield 81%.

Step 2

Synthesis of t-butyl (R)-(1-(4-amino-5-iodo-7H-pyrrolo[2,3-d]pyrimidin-7-yl) but-3-en-2-yl)carbamate

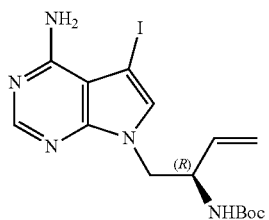

Triphenylphosphine (787 mg, 3 mmol) was added into a reaction flask, then 15 mL of anhydrous THF was added as solvent, and the resultant was cooled to 0° C. Diisopropyl azodicarboxylate (DIAD) (606 mg, 3 mmol) was added dropwise, and stirred at this temperature for 15 min, then t-butyl (R)-(1-hydroxybut-3-en-2-yl)carbamate (562 mg, 3 mmol) was added, followed by addition of 4-amino-5-iodo-7H-pyrrolo[2,3-d]pyrimidine (520 mg, 2 mmol). 30 min later, the reaction mixture was warmed to room temperature and stirred for 12 h. The insolubles were filtered off, the filtrate was concentrated, and the crude was purified by column chromatography with CHCl$_3$/MeOH=30/1 to give 308 mg of target product, yield 35.9%.

Step 3

Synthesis of t-butyl (R)-(1-(4-amino-5-(4-(phenoxyphenyl)-7H-pyrrolo[2,3-d]pyrimidin-7-yl) but-3-en-2-yl)carbamate

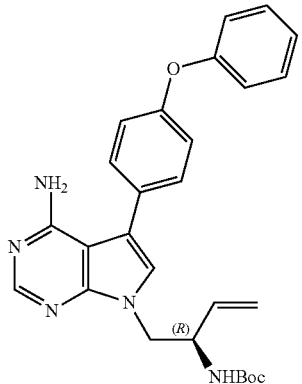

t-butyl (R)-(1-(4-amino-5-iodo-7H-pyrrolo[2,3-d]pyrimidin-7-yl)but-3-en-2-yl)carbamate (859 mg, 2 mmol), 4-phenoxyphenylboronic acid (642 mg, 3 mmol), Pd(PPh$_3$)$_4$ (116 mg, 0.1 mmol) and K$_2$CO$_3$ (553 mg, 4 mmol) were added in a sealed tube, 25 mL of 1,4-dioxane and 5 mL of water were added as the solvent, the reaction was conducted in the sealed tube under N$_2$ at 90° C. in an oil bath for 2 h. After completion of the reaction, the resultant was extracted by ethyl acetate and dried over anhydrous Na$_2$SO$_4$. The crude was purified by column chromatography with PE/EA=2/1 to give 493 mg of target product, yield 52.3%.

Step 4

Synthesis of t-butyl (R)-(1-(4-amino-5-(4-(phenoxyphenyl)-6-bromo-7H-pyrrolo[2,3-d]pyrimidin-7-yl) but-3-en-2-yl)carbamate

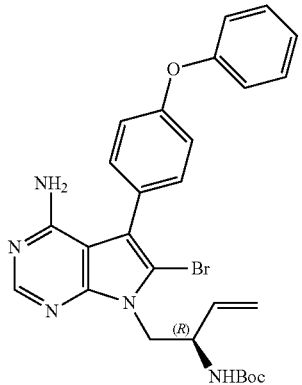

t-butyl (R)-(1-(4-amino-5-(4-(phenoxyphenyl)-7H-pyrrolo[2,3-d]pyrimidin-7-yl) but-3-en-2-yl)carbamate (943 mg, 2 mmol) was added to 50 mL of DMF, NBS (356 mg, 2 mmol) was added slowly, the reaction was stirred at room temperature for 8 h. After completion of the reaction, the resultant was extracted by ethyl acetate and dried over anhydrous Na$_2$SO$_4$. The crude was purified by column chromatography with PE/EA=2/1 to give 1.05 g of target product, yield 95.4%.

Step 5

Synthesis of t-butyl (R)-(4-amino-5-(4-phenoxyphenyl)-6,7,8,9-tetrahydropyrimido[5,4-b]indolizine-8-yl) carbamate

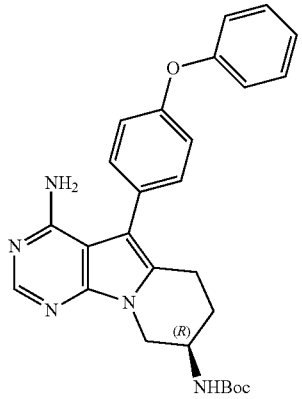

t-butyl (R)-(1-(4-amino-5-(4-(phenoxyphenyl)-6-bromo-7H-pyrrolo[2,3-d]pyrimidin-7-yl) but-3-en-2-yl)carbamate (550 mg, 1 mmol) was added to a sealed tube, 10 mL of anhydrous THF was added under N$_2$, and cooled to 0° C. A solution of 9-BBN in tetrahydrofuran (12 mL, 0.5 M) was added dropwise, and the mixture was stirred at 0° C. for 10 min, and then at room temperature for 5 h. NaOH aqueous solution (4.7 mL, 3 M) and PdCl$_2$(dppf)(190 mg, 0.25 mmol) were added successively, the reaction was conducted at 80° C. in the sealed tube for 15 h. After completion of the reaction, the resultant was extracted by ethyl acetate and dried over anhydrous Na$_2$SO$_4$. The crude was purified by column chromatography with EA to give 316 mg of target product, yield 67.0%.

Step 6

Synthesis of (R)—N-(4-amino-5-(4-phenoxyphenyl)-6,7,8,9-tetrahydropyrimido[5,4-b]indolizine-8-yl)acrylamide (S1)

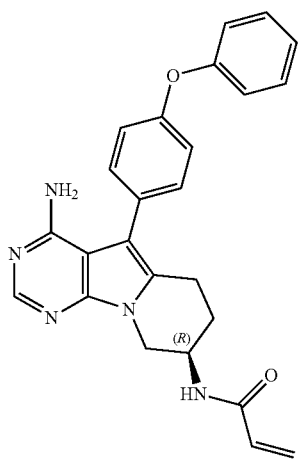

t-butyl (R)-(4-amino-5-(4-phenoxyphenyl)-6,7,8,9-tetrahydropyrimido[5,4-b]indolizine-8-yl) carbamate (472 mg, 1 mmol) was dissolved in 15 mL of methanol, a solution of HCl in methanol (5 mL, 2 M) was added dropwise at 0° C., the reaction was warmed to room temperature and stirred for 8 h. After the reaction solution was concentrated and rotated to dryness, 20 mL of DCM was directly added, followed by dropwise addition of Et$_3$N (280 µL, 2 mmol) and acrylic acid (75 µL, 1.1 mmol), HATU (418 mg, 1.1 mmol) was added and the reaction was conducted under room temperature for 2 h. After completion of the reaction, the resultant was extracted by ethyl acetate and dried over anhydrous Na$_2$SO$_4$. The crude was purified by column chromatography with CHCl$_3$/MeOH=30/1 to give 129 mg of target product, yield 30.3%.

$^1$H NMR (300 MHz, CDCl$_3$) δ 8.12 (s, 1H), 7.38 (dd, J=14.2, 7.3 Hz, 4H), 7.16 (t, J=7.2 Hz, 1H), 7.09 (d, J=8.1 Hz, 4H), 6.78 (d, J=6.7 Hz, 1H), 6.38 (d, J=16.4 Hz, 1H), 6.24 (dd, J=16.9, 10.0 Hz, 1H), 5.69 (d, J=9.8 Hz, 1H), 5.04 (s, 2H), 4.72 (br, 1H), 4.36 (dd, J=12.7, 4.6 Hz, 1H), 4.16 (dd, J=12.7, 5.7 Hz, 1H), 2.97 (t, J=6.2 Hz, 2H), 2.16-2.04 (m, 2H).

Example 2: S2

(S)—N-(4-amino-5-(4-phenoxyphenyl)-6,7,8,9-tetrahydropyrimido[5,4-b]indolizine-8-yl)acrylamide

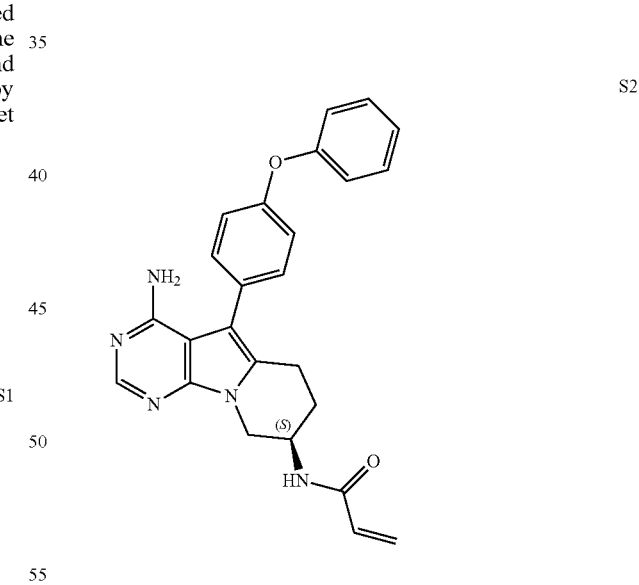

The S2 was synthesized by referring to the synthesis steps of the S1 in Example 1, except that in step 2, t-butyl (S)-(1-hydroxybut-3-en-2-yl)carbamate was used instead of t-butyl (R)-(1-hydroxybut-3-en-2-yl)carbamate.

$^1$H NMR (300 MHz, CDCl$_3$) δ 8.11 (s, 1H), 7.38 (dd, J=14.2, 7.3 Hz, 4H), 7.15 (t, J=7.2 Hz, 1H), 7.09 (d, J=8.1 Hz, 4H), 6.78 (d, J=6.7 Hz, 1H), 6.37 (d, J=16.4 Hz, 1H), 6.23 (dd, J=16.9, 10.0 Hz, 1H), 5.67 (d, J=9.8 Hz, 1H), 5.08 (s, 2H), 4.70 (br, 1H), 4.35 (dd, J=12.7, 4.6 Hz, 1H), 4.16 (dd, J=12.7, 5.7 Hz, 1H), 2.95 (t, J=6.2 Hz, 2H), 2.15-2.02 (m, 2H).

Example 3: S3

N-(4-amino-5-(4-phenoxyphenyl)-6,7,8,9-tetrahydropyrimido[5,4-b]indolizine-8-yl)acrylamide

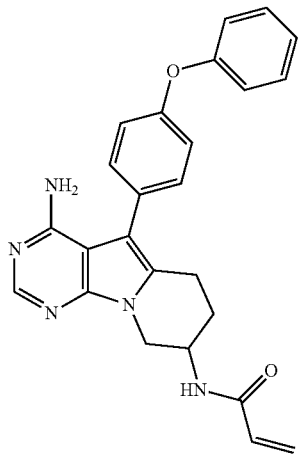

The S3 was synthesized by referring to the synthesis steps of the S1 in Example 1, except that in step 2, racemic t-butyl (1-hydroxybut-3-en-2-yl)carbamate was used instead of t-butyl (R)-(1-hydroxybut-3-en-2-yl)carbamate.

$^1$H NMR (300 MHz, CDCl$_3$) δ 8.11 (s, 1H), 7.38 (dd, J=14.2, 7.3 Hz, 4H), 7.15 (t, J=7.2 Hz, 1H), 7.08 (d, J=8.1 Hz, 4H), 6.77 (d, J=6.7 Hz, 1H), 6.36 (d, J=16.4 Hz, 1H), 6.23 (dd, J=16.9, 10.0 Hz, 1H), 5.69 (d, J=9.8 Hz, 1H), 5.10 (s, 2H), 4.72 (s, br, 1H), 4.35 (dd, J=12.7, 4.6 Hz, 1H), 4.15 (dd, J=12.7, 5.7 Hz, 1H), 2.96 (t, J=6.2 Hz, 2H), 2.16-2.03 (m, 2H).

Example 4: S4

(R)—N-(4-amino-5-(4-phenoxyphenyl)-6,7,8,9-tetrahydropyrimido[5,4-b]indolizine-8-yl)-2-cyano-4,4-dimethylpent-2-enamide

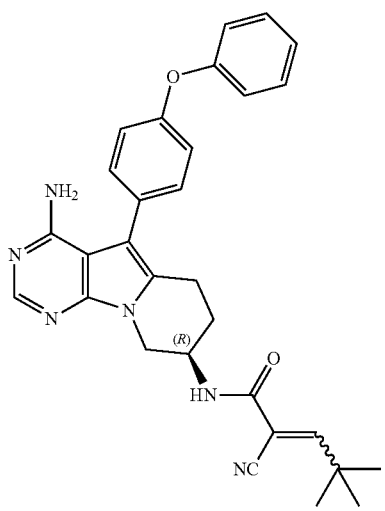

The S4 was synthesized by referring to the synthesis steps of the S1 in Example 1, except that in step 6, 2-cyano-4,4-dimethyl-2-pentenoic acid was used instead of acrylic acid.

$^1$H NMR (300 MHz, CDCl$_3$) δ 8.28 (s, 1H), 7.43-7.29 (m, 4H), 7.16 (t, J=7.3 Hz, 1H), 7.09 (d, J=8.3 Hz, 4H), 5.05 (s, 2H), 4.72 (dd, J=12.6, 5.7 Hz, 1H), 4.58-4.40 (m, 1H), 3.79 (d, J=2.9 Hz, 2H), 3.65 (d, J=2.9 Hz, 1H), 3.11 (dt, J=17.3, 4.3 Hz, 1H), 2.86 (ddd, J=16.7, 11.3, 5.2 Hz, 1H), 2.45 (ddd, J=16.5, 12.0, 5.4 Hz, 1H), 2.23 (dd, J=12.4, 4.0 Hz, 1H), 1.97 (s, 1H), 1.09 (s, 9H).

Example 5: S5

(R,E)-N-(4-amino-5-(4-phenoxyphenyl)-6,7,8,9-tetrahydropyrimido[5,4-b]indolizine-8-yl)-4-(dimethylamino)but-2-enamide

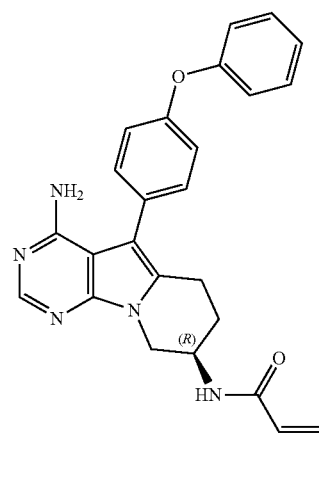

The S5 was synthesized by referring to the synthesis steps of the S1 in Example 1, except that in step 6, (E)-4-dimethylamino-2-butenoic acid was used instead of acrylic acid.

$^1$H NMR (300 MHz, CDCl$_3$) δ 8.10 (s, 1H), 7.42-7.28 (m, 5H), 7.15 (t, J=7.5 Hz, 1H), 7.07 (dd, J=7.5, 5.2 Hz, 4H), 6.94-6.80 (m, 1H), 6.29 (d, J=15.2 Hz, 1H), 5.24 (s, 2H), 4.65 (dd, J=10.4, 5.6 Hz, 1H), 4.36 (dd, J=11.9, 4.3 Hz, 1H), 4.11 (dd, J=12.9, 5.6 Hz, 1H), 3.36 (d, J=6.1 Hz, 2H), 3.04-2.88 (m, 2H), 2.49 (s, 6H), 2.07 (d, J=4.7 Hz, 2H).

Example 6: S6

(R)—N-(2-((4-amino-5-(4-phenoxyphenyl)-6,7,8,9-tetrahydropyrimido[5,4-b]indolizine-8-yl)amino)-2-oxoethyl)acrylamide

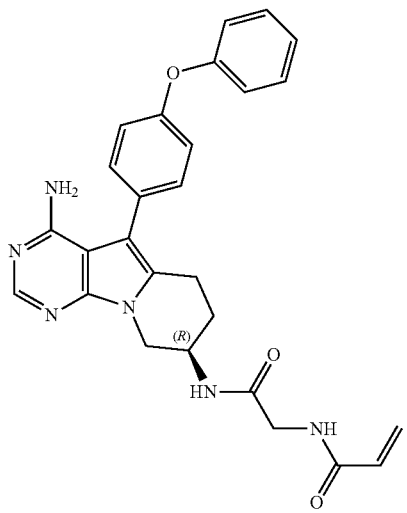

S6

The S6 was synthesized by referring to the synthesis steps of the S1 in Example 1, except that in step 6, 2-acrylamidoacetic acid was used instead of acrylic acid.

¹H NMR (300 MHz, CDCl₃) δ 8.12 (s, 1H), 7.44-7.30 (m, 4H), 7.16 (t, J=7.3 Hz, 1H), 7.13-7.01 (m, 4H), 6.36-6.07 (m, 2H), 5.67 (d, J=9.8 Hz, 1H), 5.41 (s, 2H), 4.58-4.46 (m, 1H), 4.37 (dd, J=12.7, 4.8 Hz, 1H), 4.02 (dd, J=12.7, 6.1 Hz, 3H), 3.11-2.82 (m, 2H), 2.17-1.90 (m, 2H).

Example 7: S7

N-(1-(((R)-4-amino-5-(4-phenoxyphenyl)-6,7,8,9-tetrahydropyrimido[5,4-b]indolizine-8-yl)imino)-1-oxoprop-2-yl) acrylamide

S7

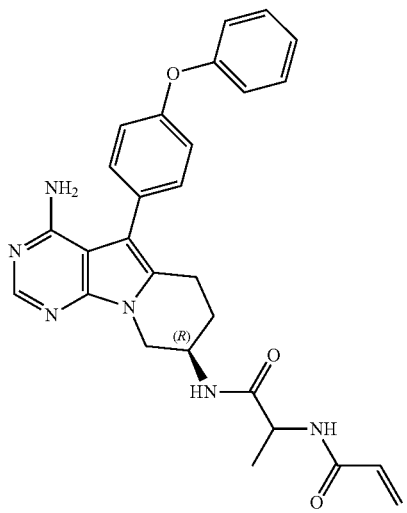

The S7 was synthesized by referring to the synthesis steps of the S1 in Example 1, except that in step 6, 2-acrylamidopropionic acid was used instead of acrylic acid.

¹H NMR (300 MHz, CDCl₃) δ 8.17 (s, 1H), 7.49-7.35 (m, 4H), 7.21 (t, J=7.3 Hz, 1H), 7.17-7.04 (m, 4H), 6.41-6.12 (m, 2H), 5.70 (d, J=9.8 Hz, 1H), 5.26 (s, 2H), 4.62-4.46 (m, 2H), 4.39 (dd, J=12.7, 4.8 Hz, 1H), 4.03 (dd, J=12.7, 5.7 Hz, 1H), 3.16-2.87 (m, 2H), 2.21-1.94 (m, 2H), 1.48 (d, J=4.5 Hz, 3H).

Example 8: S8

(R)-1-acrylamido-N-(4-amino-5-(4-phenoxyphenyl)-6,7,8,9-tetrahydropyrimido[5,4-b]indolizine-8-yl)cyclopropanecarboxamide

S8

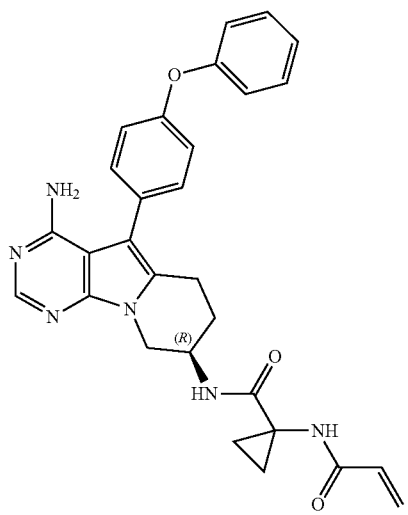

The S8 was synthesized by referring to the synthesis steps of the S1 in Example 1, except that in step 6, 1-acrylamidocyclopropanecarboxylic acid was used instead of acrylic acid.

¹H NMR (300 MHz, CDCl₃) δ 8.12 (s, 1H), 7.44-7.30 (m, 4H), 7.16 (t, J=7.3 Hz, 1H), 7.13-7.01 (m, 4H), 6.36-6.07 (m, 2H), 5.67 (d, J=9.8 Hz, 1H), 5.41 (s, 2H), 4.58-4.46 (m, 1H), 4.37 (dd, J=12.7, 4.8 Hz, 1H), 4.02 (dd, J=12.7, 6.1 Hz, 3H), 3.11-2.82 (m, 2H), 2.17-1.90 (m, 2H), 1.26-1.18 (m, 2H), 1.00-0.88 (m, 2H).

Example 9: S9

(R)—N-(4-amino-5-(4-phenoxyphenyl)-6,7,8,9-tetrahydropyrimido[5,4-b]indolizine-8-yl)vinylsulfamide

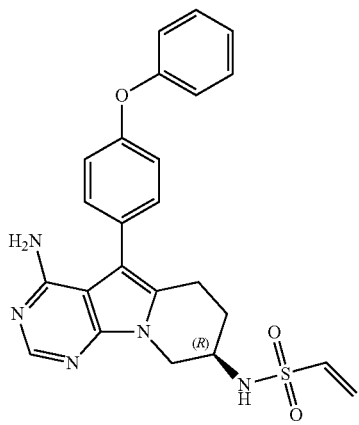

t-butyl (R)-(4-amino-5-(4-phenoxyphenyl)-6,7,8,9-tetrahydropyrimido[5,4-b]indolizine-8-yl) carbamate (472 mg, 1 mmol) (prepared according to the step 1-5 in Example 1) was dissolved in 15 mL of methanol, a solution of HCl in methanol (5 mL, 2 M) was added dropwise at 0° C., the reaction was warmed to room temperature with stirring for 8 h. After the reaction solution was concentrated and rotated to dryness, 20 mL of DCM was directly added, followed by addition of Et$_3$N (280 μL, 2 mmol) and vinylsulfonyl chloride (138 mg, 1.1 mmol), and the reaction was conducted under room temperature for 2 h. After completion of the reaction, the resultant was extracted by ethyl acetate and dried over anhydrous Na$_2$SO$_4$. The crude was purified by column chromatography with CHCl$_3$/MeOH=30/1 to give 115 mg of target product, yield 24.9%.

$^1$H NMR (300 MHz, CDCl$_3$) δ 8.12 (s, 1H), 7.38 (dd, J=14.2, 7.3 Hz, 4H), 7.16 (t, J=7.2 Hz, 1H), 7.09 (d, J=8.1 Hz, 4H), 6.78 (d, J=6.7 Hz, 1H), 6.38 (d, J=16.4 Hz, 1H), 6.24 (dd, J=16.9, 10.0 Hz, 1H), 5.69 (d, J=9.8 Hz, 1H), 5.04 (s, 2H), 4.72 (br, 1H), 4.36 (dd, J=12.7, 4.6 Hz, 1H), 4.16 (dd, J=12.7, 5.7 Hz, 1H), 2.97 (t, J=6.2 Hz, 2H), 2.16-2.04 (m, 2H).

Example 10: S10

(R)—N-(4-amino-5-(4-phenoxyphenyl)-6,7,8,9-tetrahydropyrimido[5,4-b]indolizine-8-yl)But-2-ynylamide

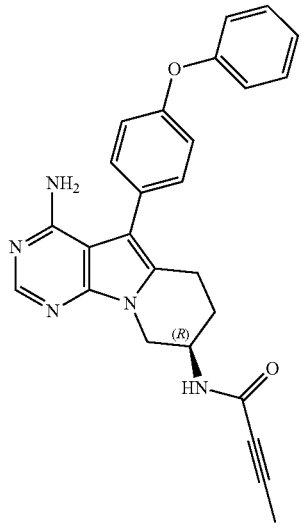

The S10 was synthesized by referring to the synthesis steps of the S1 in Example 1, except that in step 6, But-2-ynoic acid was used instead of acrylic acid.

$^1$H NMR (300 MHz, CDCl$_3$) δ 8.14 (s, 1H), 7.31 (dd, J=16.2, 8.4 Hz, 4H), 7.10 (t, J=7.8 Hz, 1H), 7.02 (d, J=8.1 Hz, 4H), 6.50 (d, J=7.5 Hz, 1H), 4.94 (s, 2H), 4.58 (dd, J=12.4, 5.3 Hz, 1H), 4.31 (dd, J=13.0, 4.7 Hz, 1H), 4.04 (dd, J=12.9, 5.8 Hz, 1H), 2.91 (t, J=6.2 Hz, 2H), 2.01 (dd, J=10.6, 5.0 Hz, 2H), 1.87 (s, 3H).

Example 11: S11

(R)—N-(4-amino-5-(4-(4-fluorophenoxy)phenyl)-6,7,8,9-tetrahydropyrimido[5,4-b]indolizine-8-yl)acrylamide

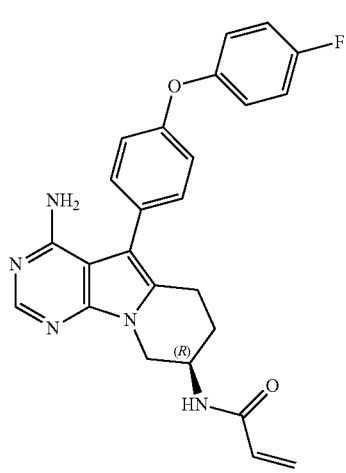

The S11 was synthesized by referring to the synthesis steps of the S1 in Example 1, except that in step 3, 4-(4-fluorophenoxy)phenylboronic acid was used instead of 4-phenoxyphenylboronic acid.

¹H NMR (300 MHz, CDCl₃) δ 8.12 (s, 1H), 7.38 (dd, J=14.2, 7.3 Hz, 4H), 7.16 (t, J=7.2 Hz, 1H), 7.09 (d, J=8.1 Hz, 4H), 6.78 (d, J=6.7 Hz, 1H), 6.38 (d, J=16.4 Hz, 1H), 6.24 (dd, J=16.9, 10.0 Hz, 1H), 5.69 (d, J=9.8 Hz, 1H), 5.04 (s, 2H), 4.72 (br, 1H), 4.36 (dd, J=12.7, 4.6 Hz, 1H), 4.16 (dd, J=12.7, 5.7 Hz, 1H), 2.97 (t, J=6.2 Hz, 2H), 2.16-2.04 (m, 2H).

Example 12: S12

(R)—N-(4-amino-5-(4-(4-(trifluoromethyl)phenoxy) phenyl)-6,7,8,9-tetrahydropyrimido[5,4-b]indolizine-8-yl)acrylamide

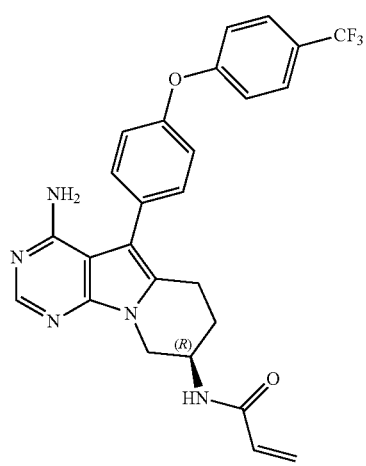

S12

The S12 was synthesized by referring to the synthesis steps of the S1 in Example 1, except that in step 3, 4-(4-trifluoromethylphenoxy)phenylboronic acid was used instead of 4-phenoxyphenylboronic acid.

¹H NMR (300 MHz, CDCl₃) δ 8.15 (s, 1H), 7.38 (dd, J=14.2, 7.3 Hz, 4H), 7.21 (d, J=8.1 Hz, 4H), 6.78 (d, J=6.7 Hz, 1H), 6.38 (d, J=16.4 Hz, 1H), 6.24 (dd, J=16.9, 10.0 Hz, 1H), 5.69 (d, J=9.8 Hz, 1H), 5.04 (s, 2H), 4.72 (br, 1H), 4.36 (dd, J=12.7, 4.6 Hz, 1H), 4.16 (dd, J=12.7, 5.7 Hz, 1H), 2.97 (t, J=6.2 Hz, 2H), 2.16-2.04 (m, 2H).

Example 13: S13

(R)-4-(8-acrylamido-4-amino-6,7,8,9-tetrahydropyrimido[5,4-b]indolizine-5-yl)-N-(pyridin-2-yl)benzamide (Scheme 3b)

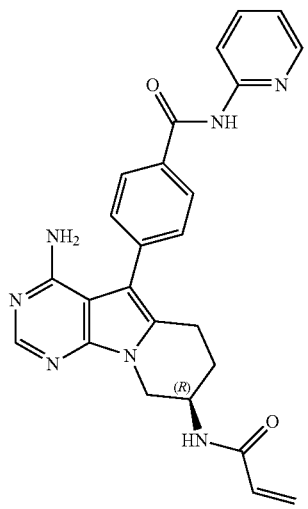

Step 1

Synthesis of methyl (R)-4-(4-amino-7-(2-((t-butoxycarbonyl)amino) but-3-en-1-yl)-7H-pyrrolo[2,3-d]pyrimidin-5-yl)benzoate

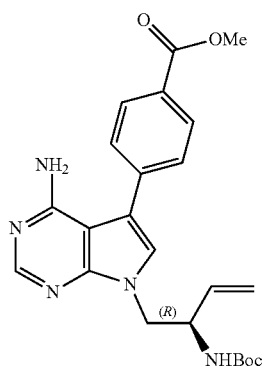

Methyl (R)-4-(4-amino-7-(2-((t-butoxycarbonyl)amino) but-3-en-1-yl)-7H-pyrrolo[2,3-d]pyrimidin-5-yl)benzoate was synthesized by referring to the step 3 in Example 1, except using 4-methoxycarbonylphenylboronic acid instead of 4-phenoxyphenylboronic acid.

Step 2

Synthesis of methyl (R)-4-(4-amino-6-bromo-7-(2-((t-butoxycarbonyl) amino)but-3-en-1-yl)-7H-pyrrolo[2,3-d]pyrimidin-5-yl)benzoate

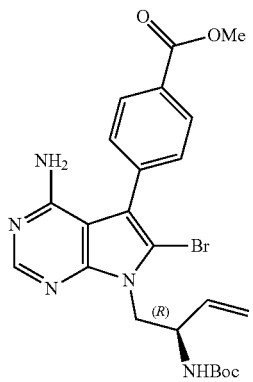

Methyl (R)-4-(4-amino-6-bromo-7-(2-((t-butoxycarbonyl)amino) but-3-en-1-yl)-7H-pyrrolo[2,3-d]pyrimidin-5-yl)benzoate was synthesized by referring to the step 4 in Example 1, except using the compound obtained from the step 1 of the present Example 13 instead of the corresponding compound in the step 4 of Example 1.

Step 3

Synthesis of methyl (R)-4-(4-amino-8-((t-butoxycarbonyl) amino)-6,7,8,9-tetrahydropyrimido[5,4-b] indolizine-5-yl)benzoate

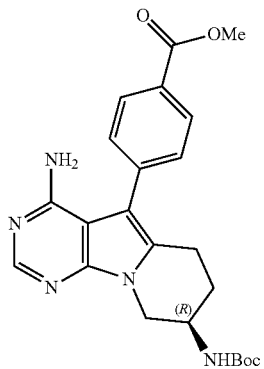

Methyl (R)-4-(4-amino-8-((t-butoxycarbonyl)amino)-6,7,8,9-tetrahydropyrimido[5,4-b]indolizine-5-yl)benzoate was synthesized by referring to the step 5 in Example 1, except using the compound obtained from the step 2 of the present Example 13 instead of the corresponding compound in the step 5 of Example 1.

Step 4

Synthesis of (R)-4-(4-amino-8-((t-butoxycarbonyl) amino)-6,7,8,9-tetrahydropyrimido[5,4-b]indolizine-5-yl)benzoic Acid

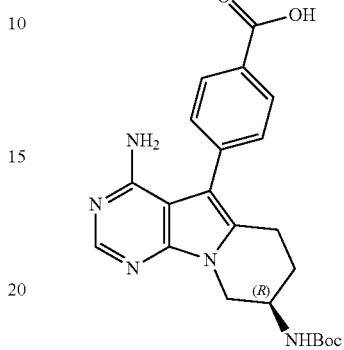

Methyl (R)-4-(4-amino-8-((t-butoxycarbonyl)amino)-6,7,8,9-tetrahydropyrimido[5,4-b]indolizine-5-yl)benzoate (437 mg, 1 mmol) was added in 10 mL methanol/10 mL water, lithium hydroxide (72 mg, 3 mmol) was added, the reaction was stirred at room temperature for 12 h. After completion of the reaction, dilute hydrochloric acid was added to adjust the pH to be neutral, 330 mg of crude was obtained by filtration, yield 77.9%.

Step 5

Synthesis of t-butyl (R)-(4-amino-5-(4-(pyridin-2-ylcarbamoyl) phenyl)-6,7,8,9-tetrahydropyrimido[5,4-b]indolizine-8-yl)carbamate

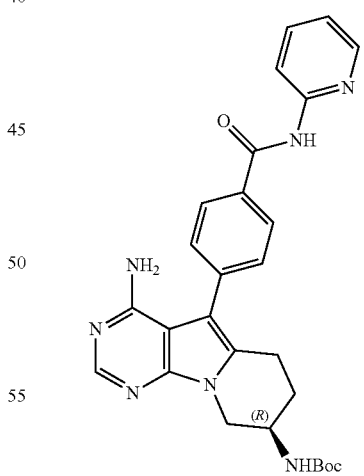

(R)-4-(4-amino-8-((t-butoxycarbonyl)amino)-6,7,8,9-tetrahydropyrimido[5,4-b]indolizine-5-yl)benzoic acid (423 mg, 1 mmol) was added to 20 mL of DCM as solvent, followed by dropwise addition of Et$_3$N (280 μL, 2 mmol) and 2-aminopyridine (104 mg, 1.1 mmol) in sequence, 2-(7-oxobenzotriazole)-N,N,N',N'-tetramethylurea hexafluorophosphate (HATU) (418 mg, 1.1 mmol) was added, the reaction was conducted at room temperature for 8 h. After completion of the reaction, the resultant was extracted by EA and dried over anhydrous Na$_2$SO$_4$. The crude was purified by column chromatography with CHCl$_3$/MeOH=30/1 to give 264 mg of target product, yield 52.8%.

Step 6

Synthesis of (R)-4-(8-acrylamido-4-amino-6,7,8,9-tetrahydropyrimido[5,4-b]indolizine-5-yl)-N-(pyridin-2-yl)benzamide(S13)

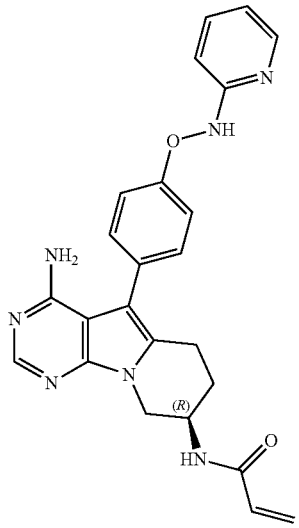

The S13 was synthesized by referring to the step 6 in Example 1, except using the compound obtained from the step 5 of the present Example 13 instead of the corresponding compound in the step 6 of Example 1.

$^1$H NMR (300 MHz, CDCl$_3$) δ 9.15 (s, 1H), 8.38 (d, J=8.4 Hz, 1H), 8.28 (d, br, 1H), 8.20 (s, 1H), 7.77 (t, br, 1H), 7.44-7.30 (m, 4H), 7.08 (ddd, J=7.3, 4.9, 0.9 Hz, 1H), 6.78 (s, 1H), 6.38 (d, J=16.4 Hz, 1H), 6.24 (dd, J=16.9, 10.0 Hz, 1H), 5.69 (d, J=9.8 Hz, 1H), 5.20 (s, 2H), 4.72 (br, 1H), 4.36 (dd, J=12.7, 4.6 Hz, 1H), 4.16 (dd, J=12.7, 5.7 Hz, 1H), 2.97 (t, J=6.2 Hz, 2H), 2.16-2.04 (m, 2H).

Example 14: S14

(R)-4-(4-amino-8-(but-2-ynylamide)-6,7,8,9-tetrahydropyrimido[5,4-b]indolizine-5-yl)-N-(pyridin-2-yl)benzamide

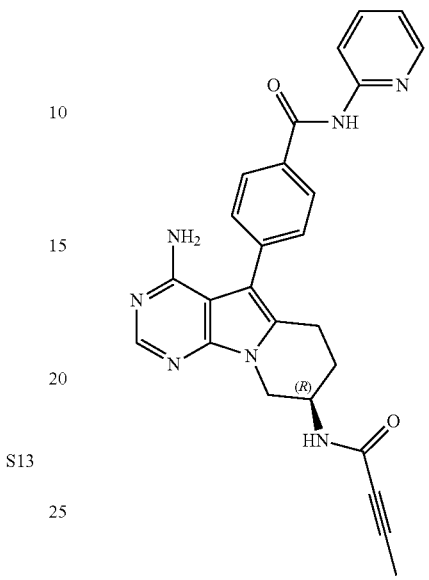

The S14 was synthesized by referring to the step 6 in Example 1, except using the compound obtained from the step 5 of the present Example 13 instead of the corresponding compound in the step 6 of Example 1, and using but-2-ynoic acid instead of acrylic acid in the step 6 of Example 1.

$^1$H NMR (300 MHz, CDCl$_3$) δ 9.20 (s, 1H), 8.38 (d, J=8.4 Hz, 1H), 8.27 (d, br, 1H), 8.19 (s, 1H), 7.75 (t, br, 1H), 7.44-7.30 (m, 4H), 7.08 (ddd, J=7.3, 4.9, 0.9 Hz, 1H), 6.70 (s, 1H), 4.57 (dd, J=12.4, 5.3 Hz, 1H), 4.30 (dd, J=13.0, 4.7 Hz, 1H), 4.03 (dd, J=12.9, 5.8 Hz, 1H), 2.91 (t, J=6.2 Hz, 2H), 2.02 (dd, J=10.6, 5.0 Hz, 2H), 1.86 (s, 3H).

Example 15: S15

(R)-4-(8-acrylamido-4-amino-6,7,8,9-tetrahydropyrimido[5,4-b]indolizine-5-yl)-N-(5-fluoropyridin-2-yl)benzamide

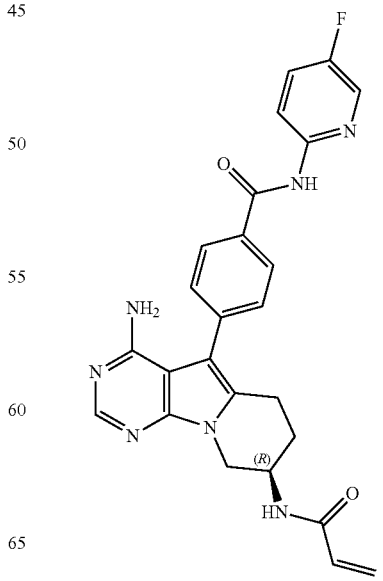

The S15 was synthesized by referring to the synthesis steps of the S13 in Example 13, except using 2-amino-5-fluoropyridine instead of 2-aminopyridine in the step 5 of Example 13.

$^1$H NMR (300 MHz, CDCl$_3$) δ 8.90 (s, 1H), 8.28 (d, J=8.0 Hz, 1H), 8.17 (s, 1H), 8.04 (s, 1H), 7.85 (d, J=8.0 Hz, 2H), 7.65 (d, J=8.0 Hz, 2H), 7.59 (d, J=8.0 Hz, 1H), 6.78 (s, 1H), 6.38 (d, J=16.4 Hz, 1H), 6.24 (dd, J=16.9, 10.0 Hz, 1H), 5.69 (d, J=9.8 Hz, 1H), 5.20 (s, 2H), 4.72 (br, 1H), 4.36 (dd, J=12.7, 4.6 Hz, 1H), 4.16 (dd, J=12.7, 5.7 Hz, 1H), 2.97 (t, J=6.2 Hz, 2H), 2.16-2.04 (m, 2H).

Example 16: S16

(R)-4-(8-acrylamido-4-amino-6,7,8,9-tetrahydropyrimido[5,4-b]indolizine-5-yl)-N-(4-(trifluoromethyl)pyridin-2-yl)benzamide

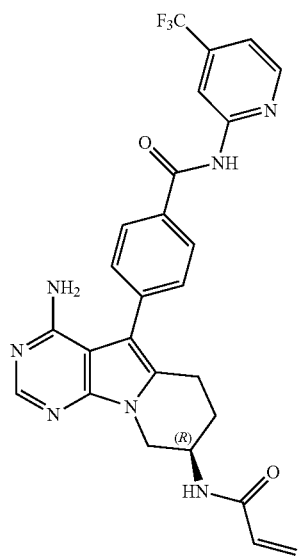

S16

The S16 was synthesized by referring to the synthesis steps of the S13 in Example 13, except using 2-amino-4-trifluoromethylpyridine instead of 2-aminopyridine in the step 5 of Example 13.

$^1$H NMR (300 MHz, CDCl$_3$) δ 8.80 (s, 1H), 8.25 (s, 1H), 8.21 (s, 1H), 8.07 (d, J=5.1 Hz, 1H), 7.86 (dd, J=6.8, 1.8 Hz, 2H), 7.45 (dd, J=6.8, 1.8 Hz, 2H), 6.89 (d, J=5 Hz, 1H), 6.78 (s, 1H), 6.38 (d, J=16.4 Hz, 1H), 6.24 (dd, J=16.9, 10.0 Hz, 1H), 5.69 (d, J=9.8 Hz, 1H), 5.20 (s, 2H), 4.72 (br, 1H), 4.36 (dd, J=12.7, 4.6 Hz, 1H), 4.16 (dd, J=12.7, 5.7 Hz, 1H), 2.97 (t, J=6.2 Hz, 2H), 2.16-2.04 (m, 2H).

Example 17: S17

4-((R)-8-acrylamido-4-amino-6,7,8,9-tetrahydropyrimido[5,4-b]indolizine-5-yl)-N—((R)-2-methoxy-1-phenylethyl)benzamide

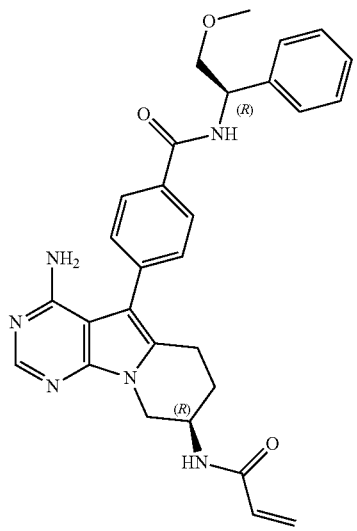

S17

The S17 was synthesized by referring to the synthesis steps of the S13 in Example 13, except using (R)-2-methoxy-1-phenylethylamine instead of 2-aminopyridine in the step 5 of Example 13.

$^1$H NMR (300 MHz, CDCl$_3$) δ 8.40 (s, 1H), 7.99 (d, J=7.9 Hz, 2H), 7.78 (d, J=7.8 Hz, 2H), 7.49-7.28 (m, 5H), 6.99 (d, J=7.0 Hz, 1H), 6.78 (d, J=6.7 Hz, 1H), 6.38 (d, J=16.4 Hz, 1H), 6.24 (dd, J=16.9, 10.0 Hz, 1H), 5.69 (d, J=9.8 Hz, 1H), 5.42-5.35 (m, 1H), 5.04 (s, 2H), 4.72 (br, 1H), 4.36 (dd, J=12.7, 4.6 Hz, 1H), 4.16 (dd, J=12.7, 5.7 Hz, 1H), 4.09 (s, 1H), 3.84 (s, 1H), 3.42 (s, 3H), 2.97 (t, J=6.2 Hz, 2H), 2.16-2.04 (m, 2H).

Example 18: S18

(R)—N-(4-amino-6-methylidene-5-(4-phenoxyphenyl)-7,8-dihydro-6H-pyrimido[5,4-b]pyrrolizin-7-yl)acrylamide (Scheme 1b)

Step 1

Synthesis of t-butyl (R)-(4-amino-6-methylidene-5-(4-phenoxyphenyl)-7,8-dihydro-6H-pyrimido[5,4-b]pyrrolizin-7-yl)carbamate

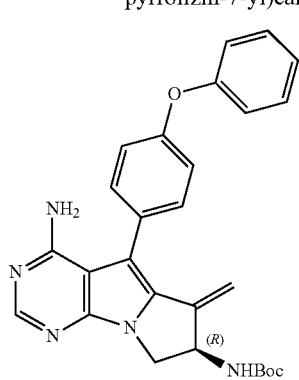

t-butyl (R)-(1-(4-amino-5-(4-phenoxyphenyl)-6-bromo-7H-pyrrolo[2,3-d]pyrimidin-7-yl)but-3-en-2-yl)carbamate (550 mg, 1 mmol)(the compound synthesized in step 4 of Example 1) was added to a sealed tube under N$_2$. 10 mL of anhydrous THF was added, then NaOH aqueous solution (4.7 mL, 3 M) and PdCl$_2$(dppf)(190 mg, 0.25 mmol) were added successively, the reaction was conducted at 80° C. for 15 h. After completion of the reaction, the resultant was extracted by ethyl acetate and dried over anhydrous Na$_2$SO$_4$. The crude was purified by column chromatography with EA to give 245 mg of target product, yield 52.0%.

Step 2

Synthesis of (R)—N-(4-amino-6-methylidene-5-(4-phenoxyphenyl)-7,8-dihydro-6H-pyrimido[5,4-b]pyrrolizin-7-yl)acrylamide (S18)

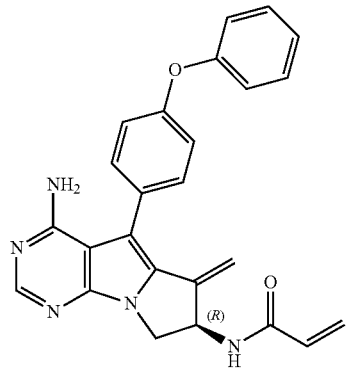

S18

The S18 was synthesized by referring to the step 6 in Example 1, except using the compound obtained from the step 1 of the Example 18 instead of the corresponding compound in the step 6 of Example 1.

$^1$H NMR (300 MHz, CDCl$_3$) δ 8.25 (s, 1H), 7.50-7.36 (m, 4H), 7.18 (t, J=7.4 Hz, 1H), 7.10 (d, J=8.4 Hz, 4H), 6.40 (d, J=16.9 Hz, 1H), 6.28-6.08 (m, 2H), 5.75 (d, J=10.4 Hz, 1H), 5.73-5.66 (m, 1H), 5.53 (s, 1H), 5.19 (s, 1H), 5.09 (s, 2H), 4.75-4.62 (m, 1H), 3.99 (dd, J=11.5, 4.7 Hz, 1H).

Example 19: S19

(R)—N-(4-amino-6-methylidene-5-(4-phenoxyphenyl)-7,8-dihydro-6H-pyrimido[5,4-b]pyrrolizin-7-yl)but-2-ynylamide

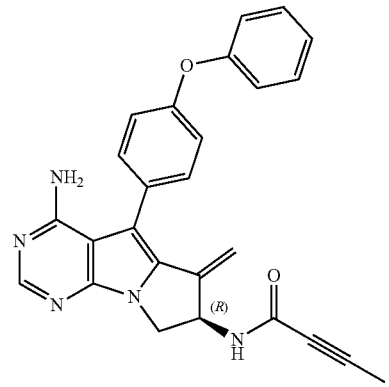

S19

The S19 was synthesized by referring to the synthesis step of the S18 in Example 18, except using the compound obtained from the step 1 of the present Example 18 instead of the corresponding compound in the step 6 of Example 1, and using but-2-ynoic acid instead of acrylic acid in the step 6 of Example 1.

$^1$H NMR (300 MHz, CDCl$_3$) δ 8.21 (s, 1H), 7.45-7.29 (m, 4H), 7.12 (t, J=7.2 Hz, 1H), 7.05 (d, J=8.1 Hz, 4H), 6.19-6.07 (m, 1H), 5.63-5.52 (m, 1H), 5.47 (s, 1H), 5.14 (s, 1H), 4.97 (s, 2H), 4.62 (dd, J=11.4, 7.8 Hz, 1H), 3.92 (dd, J=11.5, 4.7 Hz, 1H), 1.91 (s, 3H).

Example 20: S20

(R)-4-(7-acrylamido-4-amino-6-methylidene-7,8-dihydro-6H-pyrimido[5,4-b]pyrrolizin-5-yl)-N-(pyridin-2-yl)benzamide (Scheme 3b)

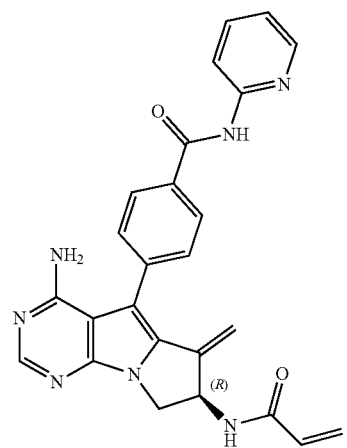

S20

-continued

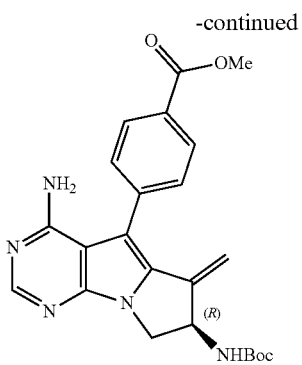

HBoc was synthesized by referring to the step 1 of the Example 18, except using methyl (R)-4-(4-amino-6-bromo-7-(2-((t-butoxycarbonyl)amino)but-3-en-1-yl)-7H-pyrrolo[2,3-d]pyrimidin-5-yl)benzoate (the compound obtained from the step 2 of the Example 13) instead of t-butyl (R)-(1-(4-amino-5-(4-phenoxyphenyl)-6-bromo-7H-pyrrolo[2,3-d]pyrimidin-7-yl)but-3-en-2-yl)carbamate (550 mg, 1 mmol)(the compound synthesized in step 4 of Example 1). Then the S20 was synthesized by referring to the step 3 to step 6 in Example 13 except using the

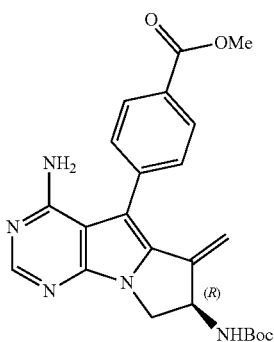

instead of the compound in the step 2 of Example 13.

$^1$H NMR (300 MHz, CDCl$_3$) δ 9.15 (s, 1H), 8.38 (d, J=8.4 Hz, 1H), 8.28 (d, br, 1H), 8.20 (s, 1H), 7.77 (t, br, 1H), 7.44-7.30 (m, 4H), 7.08 (ddd, J=7.3, 4.9, 0.9 Hz, 1H), 6.78 (s, 1H), 6.40 (d, J=16.9 Hz, 1H), 6.28-6.08 (m, 2H), 5.73-5.66 (m, 1H), 5.53 (s, 1H), 5.19 (s, 1H), 5.09 (s, 2H), 4.75-4.62 (m, 1H), 3.99 (dd, J=11.5, 4.7 Hz, 1H).

Example 21: S21

N-((7R)-4-amino-6-methyl-5-(4-phenoxyphenyl)-7,8-dihydro-6H-pyrimido[5,4-b]pyrrolizin-7-yl)acrylamide (Scheme 1c)

Step 1

Synthesis of t-butyl ((7R)-(4-amino-6-methyl-5-(4-phenoxyphenyl)-7,8-dihydro-6H-pyrimido[5,4-b]pyrrolizin-7-yl)carbamate

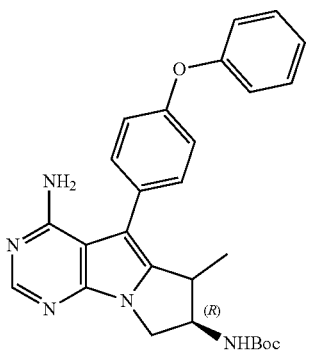

t-butyl (R)-(4-amino-6-methylidene-5-(4-phenoxyphenyl)-7,8-dihydro-6H-pyrimido[5,4-b]pyrrolizin-7-yl)carbamate (the compound obtained in step 1 of Example 18)(470 mg, 1 mmol) was added to 20 mL of methanol, Pd/C (213 mg, 0.2 mmol, 10%) was added, the reaction was stirred while introducing H$_2$ for 6 h. After completion of the reaction, Pd/C was removed by filtration. The reaction solution was separated and purified by column chromatography with CHCl$_3$/MeOH=20/1 to give 102 mg of target product, yield 21.6%.

Step 2

Synthesis of N-((7R)-4-amino-6-methyl-5-(4-phenoxyphenyl)-7,8-dihydro-6H-pyrimido[5,4-b]pyrrolizin-7-yl)acrylamide (S21)

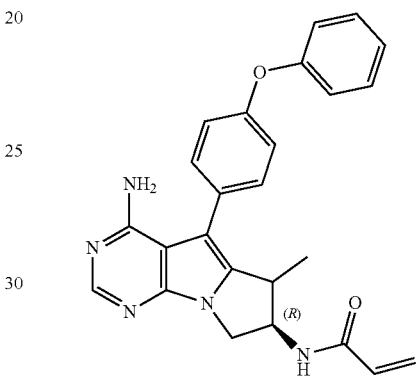

The S21 was synthesized by referring to the step 6 in Example 1, except using the compound obtained from the step 1 of the present Example 21 instead of the corresponding compound in the step 6 of Example 1.

$^1$H NMR (300 MHz, CDCl$_3$) δ 8.17 (s, 1H), 7.44-7.35 (m, 4H), 7.16 (t, J=7.4 Hz, 1H), 7.08 (dd, J=7.7, 3.7 Hz, 4H), 6.78 (s, 1H), 6.38 (d, J=16.4 Hz, 1H), 6.24 (dd, J=16.9, 10.0 Hz, 1H), 5.85 (s, 2H), 5.69 (d, J=9.8 Hz, 1H), 4.41 (dd, J=11.0, 6.7 Hz, 1H), 4.20 (dd, J=12.3, 5.8 Hz, 1H), 3.85 (dd, J=10.7, 6.2 Hz, 1H), 3.50-3.33 (m, 1H), 1.15 (d, J=7.2 Hz, 3H).

Example 22: S22

4-((7R)-7-acrylamido-4-amino-6-methyl-7,8-dihydro-6H-pyrimido[5,4-b]pyrrolizin-5-yl)-N-(pyridin-2-yl)benzamide (Scheme 4)

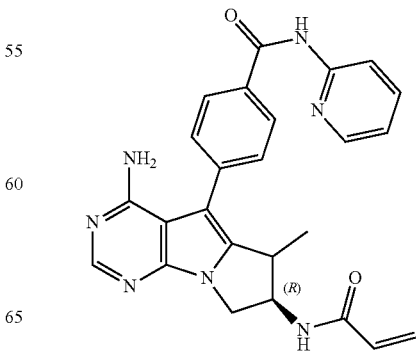

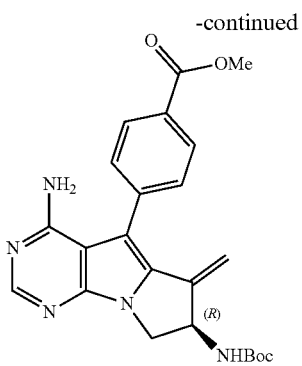

was synthesized by referring to the step 1 of the Example 18, except using methyl (R)-4-(4-amino-6-bromo-7-(2-((t-butoxycarbonyl)amino)but-3-en-1-yl)-7H-pyrrolo[2,3-d]pyrimidin-5-yl)benzoate (the compound obtained from the step 2 of the Example 13) instead of t-butyl (R)-(1-(4-amino-5-(4-phenoxyphenyl)-6-bromo-7H-pyrrolo[2,3-d]pyrimidin-7-yl)but-3-en-2-yl)carbamate (550 mg, 1 mmol)(the compound synthesized in step 4 of Example 1). Then the S22 was synthesized by referring to the step 1 to step 2 in Example 21 except using the

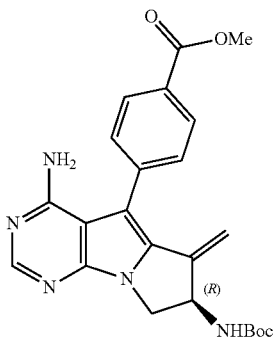

instead of t-butyl (R)-(4-amino-6-methylidene-5-(4-phenoxyphenyl)-7,8-dihydro-6H-pyrimido[5,4-b]pyrrolizin-7-yl)carbamate (the compound obtained from the step 1 of Example 18).

$^1$H NMR (300 MHz, CDCl$_3$) δ 9.15 (s, 1H), 8.38 (d, J=8.4 Hz, 1H), 8.28 (d, br, 1H), 8.20 (s, 1H), 7.77 (t, br, 1H), 7.44-7.30 (m, 4H), 7.08 (ddd, J=7.3, 4.9, 0.9 Hz, 1H), 6.78 (s, 1H), 6.38 (d, J=16.4 Hz, 1H), 6.24 (dd, J=16.9, 10.0 Hz, 1H), 5.85 (s, 2H), 5.69 (d, J=9.8 Hz, 1H), 4.41 (dd, J=11.0, 6.7 Hz, 1H), 4.20 (dd, J=12.3, 5.8 Hz, 1H), 3.85 (dd, J=10.7, 6.2 Hz, 1H), 3.50-3.33 (m, 1H), 1.15 (d, J=7.2 Hz, 3H).

Experimental Example 1: Evaluation of Inhibitory Activity Against Bruton Kinase (BTK) at Molecular Level 1. Experimental Method Poly(Glu, Tyr) 4:1 as a substrate for enzyme catalyzed reaction was diluted with potassium-free PBS (10 mM sodium phosphate buffer, 150 mM NaCl, pH 7.2-7.4) to g/mL to coat a ELISA plate. The plate was cultured at 37° C. for 12-16 h, washed with 200 μL/well of T-PBS (PBS containing 0.1% of Tween-20) three times, and dried in an oven at 37° C. for 1-2 h. Into the above ELISA plate coated with the substrate, an ATP solution diluted with a reaction buffer (50 mM HEPES, pH 7.4, 50 mM MgCl$_2$, 5 mM MnCl$_2$, 0.2 mM Na$_3$VO$_4$, 1 mM DTT) was first added at 50 μL/well (concentration of 10 μM). Then, a test compound diluted by 1% DMSO to a suitable concentration was added (10 μL/well), and negative control well and positive compound control well were provided separately. Finally, the reaction was initiated by adding BTK tyrosine kinase protein diluted in 40 μL of reaction buffer.

The above reaction system was placed on a shaker (100 rpm) at 37° C. for 1 h, then washed with T-PBS for three times, primary antibody PY99 (Cell Signaling Technology) was added at 100 μL/well, and the reaction was conducted on the shaker at 37° C. for 0.5 h. After the plate was washed with T-PBS, secondary antibody horseradish peroxidase-labeled goat anti-mouse IgG was added at 100 μL/well, and the reaction was conducted on the shaker at 37° C. for 0.5 h. After the plate was washed with T-PBS, 2 mg/mL of OPD developing solution was added at 100 μL/well, and the reaction was conducted in the dark at 25° C. for 1 to 10 minutes. Then the reaction was quenched by adding 2 M H$_2$SO$_4$ at 50 μL/well. The data were read on a wavelength-tunable microplate reader ELISA SPECTRA MAX 190 at a wavelength of 490 nm.

The inhibition rate of the compound was calculated by the following equation: inhibition rate (%)=(OD$_{control\ well}$−OD$_{administration\ well}$)/OD$_{control\ well}$×100%. IC$_{50}$ was calculated by fitting the inhibition curve using a four-parameter method.

2. Experimental Results

| Compound | IC$_{50}$ (nM) |
| --- | --- |
| S1 | <1 |
| S2 | <1 |
| S3 | <1 |
| S4 | >100 |
| S5 | <1 |
| S6 | 1~10 |
| S7 | 10~100 |
| S8 | >100 |
| S9 | 10~100 |
| S10 | 1~10 |
| S11 | <1 |
| S12 | <1 |
| S13 | 1~10 |
| S14 | 1~10 |
| S15 | 1~10 |
| S16 | 1~10 |
| S17 | 1~10 |
| S18 | 1~10 |
| S19 | <1 |
| S20 | 1~10 |
| S21 | 1~10 |
| S22 | 1~10 |

Experimental Example 2: Test on In Vitro Proliferation Inhibition Activity of Representative Compounds Against Human B Lymphoma Ramos Cells and Human Diffuse Large B Lymphoma TMD8 Cells 1. Experimental Method Cells were seeded at 10000-15000/well into a 96-well culture plate, different concentrations of a test compound were added to each well (3 replicate-wells for each concentration), and blank control, positive compound control and negative control were provided. 48 hours after the administration of the drugs, 20 ml of MTT (5 mg/ml) was added, and the plate was incubated at 37° C. for 4 h, and then 100 ml of a triad solution (10% SDS, 5% isobutanol, 0.01 M HCl) was added. The resultant was cultured at 37° C. overnight, and the OD value was measured at a wavelength of 570 nm using a wavelength-tunable microplate reader ELISA SPECTRA MAX 190. The inhibition rate of the compound was calculated by the following equation: inhibition rate (%)=(OD$_{control\ well}$–OD$_{administration\ well}$)/OD$_{control\ well}$×100%. The IC$_{50}$ value was calculated by fitting the inhibition curve using a four-parameter method. The experiment was repeated 3 times independently.

2. Experimental Results (1) Inhibition Activity Against Proliferation of Human B Lymphoma Ramos Cells of Representative Compounds

| Compound | IC$_{50}$ for proliferation of Ramos cells |
| --- | --- |
| S1 | 94.73 ± 45.06 μM |
| S3 | 11.4 ± 0.8 μM |
| S5 | 6.6 ± 2.1 μM |
| S6 | 5.5 ± 1.0 μM |
| S10 | 8.72 ± 8.58 μM |
| S19 | 16.9 ± 7.9 μM |
| Ibrutinib | ~8.53 μM |

(2) Inhibition Activity Against Proliferation of Human Diffuse Large B Lymphoma TMD8 Cells of Representative Compounds

| Compound | IC$_{50}$ for the inhibition TMD of cells |
| --- | --- |
| S1 | 0.0058 μM |
| S10 | 0.03 μM |
| Ibrutinib | 0.0045 μM |

The present invention provides a series of 5-aryl-pyrimidopyrrolizine or 5-aryl-pyrimidoindolizine tricyclic compounds. The series of derivatives are Bruton kinase inhibitors with novel structures, and some of the compounds have considerable inhibitory activities against BTK enzymes and considerable inhibitory activities against BTK-dependent TMD8 cells at molecular level. And it is more important that some of the compounds (e.g., S1) shows low cell activity against human B lymphoma Ramos cells, and good selectivity to BTK, and therefore they are a class of BTK selective inhibitors with much potential.

The invention claimed is:

1. A 5-aryl-pyrimidoindolizine or 5-aryl-pyrimidopyrrolizine compound as shown in formula I or a pharmaceutically acceptable salt thereof,

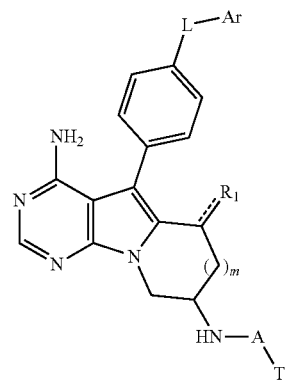

Formula I wherein:
R$_1$ is H, methyl or methylidene;
L is —O—, —C(=O)NH— or —C(=O)NHCHR$_2$—, wherein, R$_2$ is hydrogen or substituted or unsubstituted C1-C3 alkyl, wherein, the substituent in R$_2$ is halogen or C1-C3 alkoxy;
m is 0 or 1;
Ar is substituted or unsubstituted C6-C20 aryl, substituted or unsubstituted 5-20 membered heteroaryl containing one or more heteroatoms selected from the group consisting of O, N and S, wherein the substituent in Ar is halogen, C1-C6 alkyl, C1-C6 alkoxy, trifluoromethyl or trifluoromethoxy,
A is carbonyl, sulfonyl, or

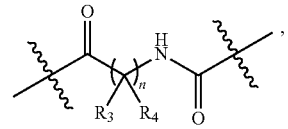

wherein R$_3$ and R$_4$ are independently hydrogen or C1-C3 alkyl, or R$_3$, R$_4$ and the carbon atom attached thereto form C3-C5 cycloalkyl;
n is 0, 1 or 2;
T is

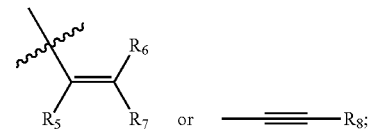

R$_5$, R$_6$ and R$_7$ are independently selected from the group consisting of hydrogen, cyano, halogen, and substituted or unsubstituted C1-C20 alkyl; the substituent in R$_5$, R$_6$ or R$_7$ is dimethylamino, C1-C10 alkoxy, or 3 to 10 membered heterocyclyl containing one or more heteroatoms selected from the group consisting of O, N and S;
R$_8$ is selected from the group consisting of hydrogen and C1-C10 alkyl.

2. The 5-aryl-pyrimidoindolizine or 5-aryl-pyrimidopyrrolizine compound or a pharmaceutically acceptable salt thereof according to claim 1,
wherein Ar is substituted or unsubstituted C6-C10 aryl, substituted or unsubstituted 5-10 membered heteroaryl containing one or more heteroatoms selected from the group consisting of O, N and S, wherein the substituent in Ar is halogen, C1-C3 alkyl, C1-C3 alkoxy, trifluoromethyl or trifluoromethoxy;
n is 0 or 1;
T is

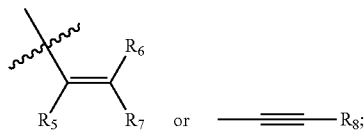

$R_5$, $R_6$ and $R_7$ are independently selected from the group consisting of hydrogen, cyano, halogen, and substituted or unsubstituted C1-C10 alkyl; the substituent in $R_5$, $R_6$ or $R_7$ is dimethylamino, C1-C5 alkoxy, or 3 to 6 membered heterocyclyl containing 1 to 3 heteroatoms selected from the group consisting of O, N and S;
$R_8$ is selected from the group consisting of hydrogen and C1-C5 alkyl.

3. The 5-aryl-pyrimidoindolizine or 5-aryl-pyrimidopyrrolizine compound or a pharmaceutically acceptable salt thereof according to claim 1,
wherein Ar is substituted or unsubstituted phenyl, substituted or unsubstituted 5 to 6-membered heteroaryl, wherein the substituent in Ar is halogen, C1-C3 alkyl, C1-C3 alkoxy, trifluoromethyl or trifluoromethoxy;
n is 0 or 1;
T is

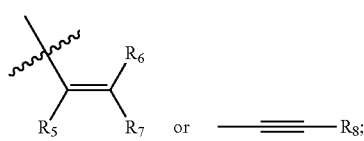

$R_5$, $R_6$ and $R_7$ are independently selected from the group consisting of hydrogen, cyano, halogen, and substituted or unsubstituted C1-C5 alkyl; the substituent in $R_5$, $R_6$ or $R_7$ is dimethylamino, C1-C5 alkoxy, or 3 to 6 membered heterocyclyl containing 1 to 3 heteroatoms selected from the group consisting of O, N and S;
$R_8$ is selected from the group consisting of hydrogen and C1-C3 alkyl.

4. The 5-aryl-pyrimidoindolizine or 5-aryl-pyrimidopyrrolizine compound or a pharmaceutically acceptable salt thereof according to claim 1,
wherein L is —O—, —C(=O)NH—,
wherein, Ar is phenyl, 4-fluorophenyl, 4-trifluoromethylphenyl, pyridin-2-yl, 3-fluoropyridin-6-yl or 4-trifluoromethylpyridine-6-yl;
wherein A is carbonyl, sulfonyl, or

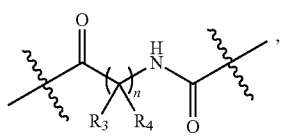

wherein n is 0 or 1, and when n is 1, $R_3$ is hydrogen, $R_4$ is H or methyl, or $R_3$, $R_4$ and the carbon atom attached thereto form cyclopropyl;

wherein T is

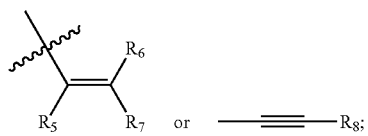

wherein $R_5$ is H, cyano or methyl, $R_6$ is H, $R_7$ is H, t-butyl or dimethylaminomethyl, $R_8$ is H or methyl.

5. The 5-aryl-pyrimidoindolizine or 5-aryl-pyrimidopyrrolizine compound or a pharmaceutically acceptable salt thereof according to claim 1, wherein the compound is selected from the group consisting of the compounds shown in the following table:

| Compound | Structure |
|---|---|
| S1 | 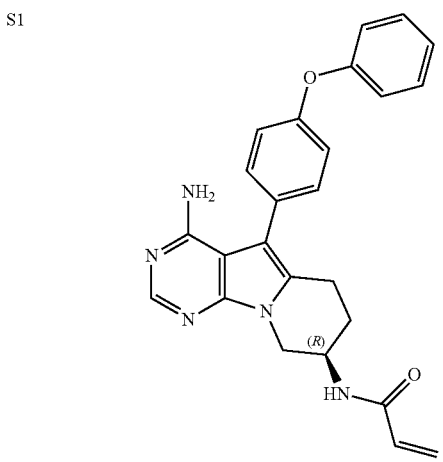 |
| S2 | 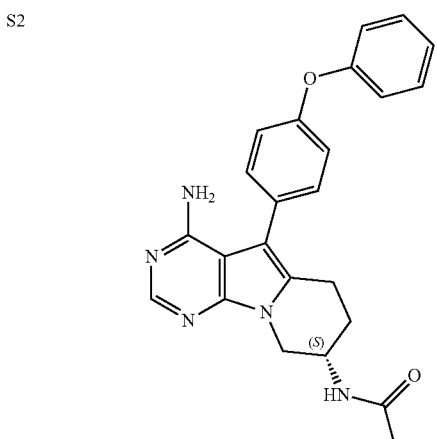 |

53
-continued
| Compound | Structure |
|---|---|
| S3 | 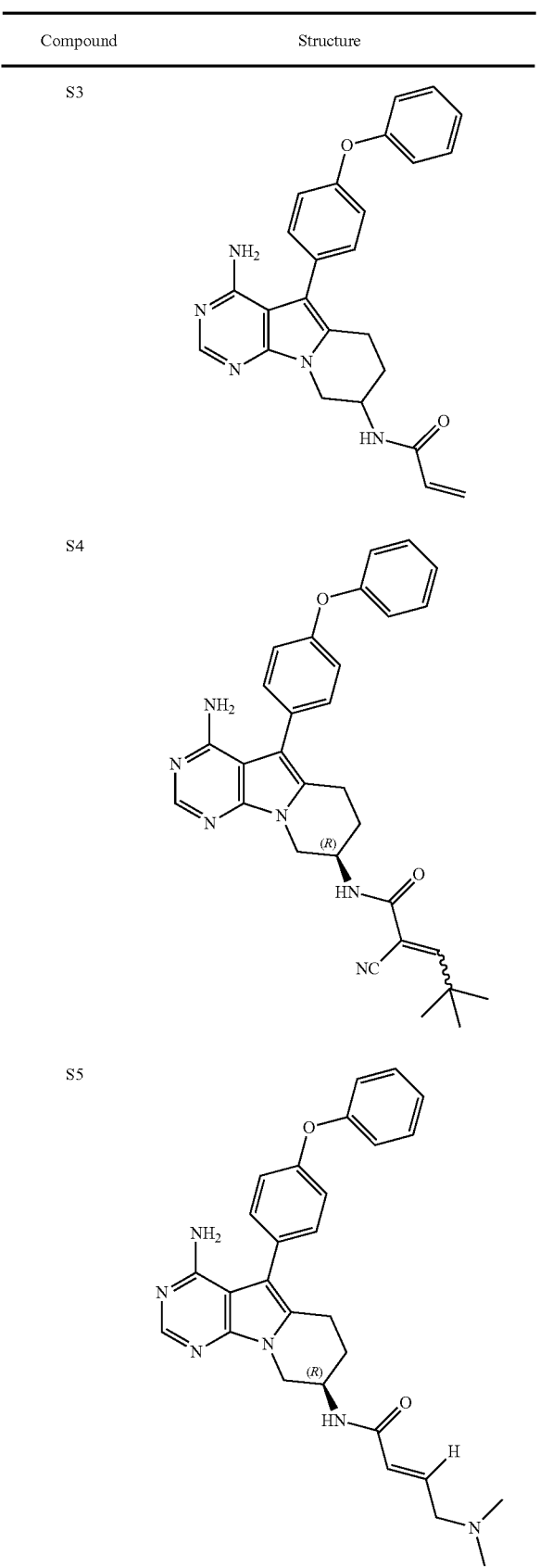 |
| S4 | 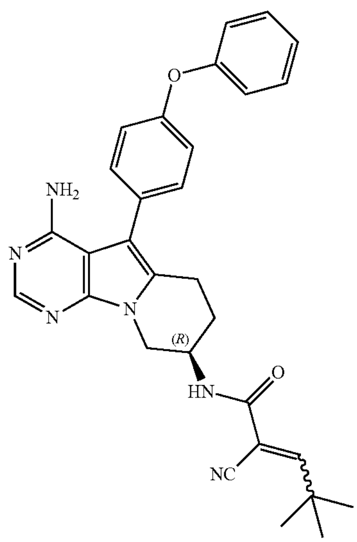 |
| S5 | 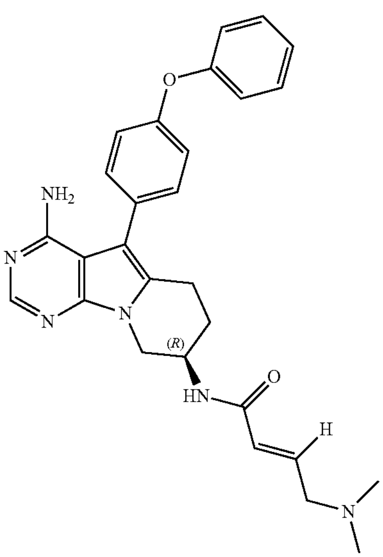 |
54
-continued
| Compound | Structure |
|---|---|
| S6 | 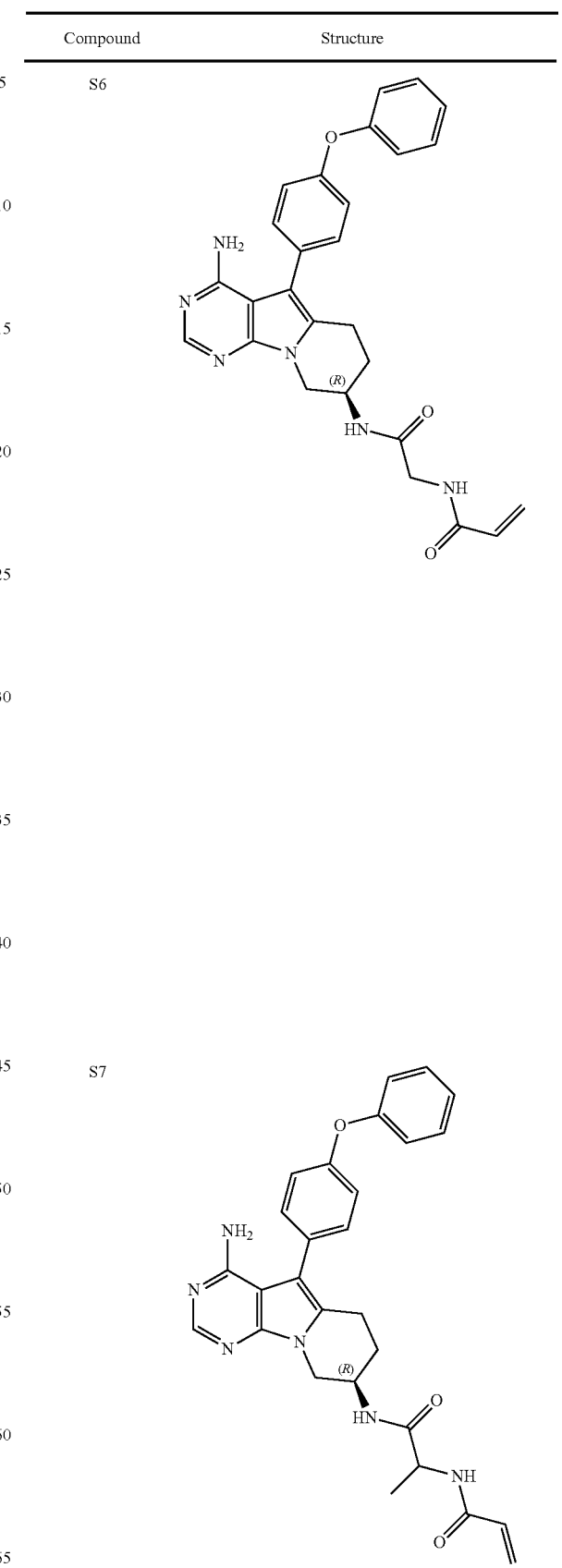 |
| S7 | 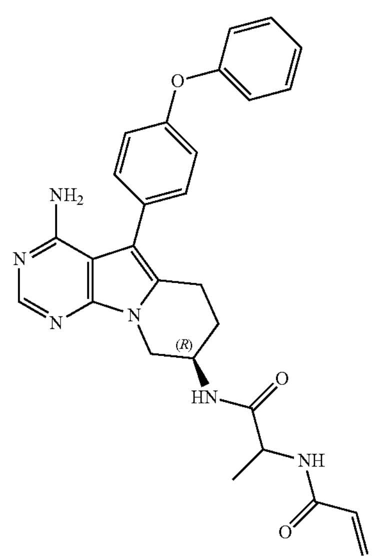 |

-continued
| Compound | Structure |
|---|---|
| S8 | 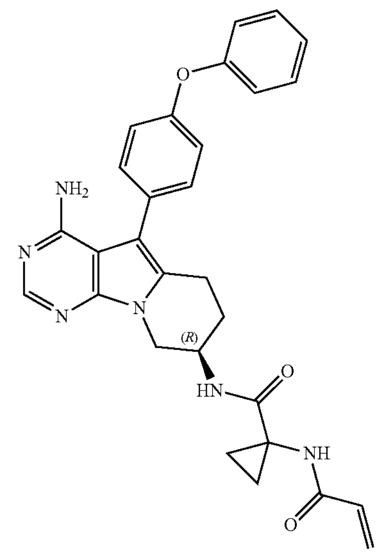 |
| S9 | 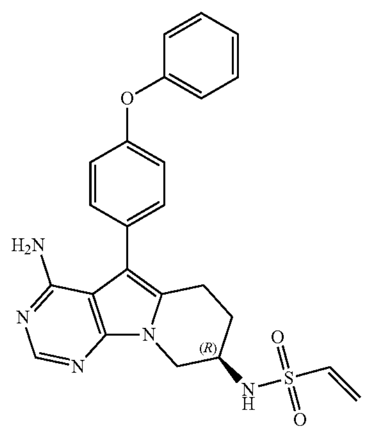 |
| S10 | 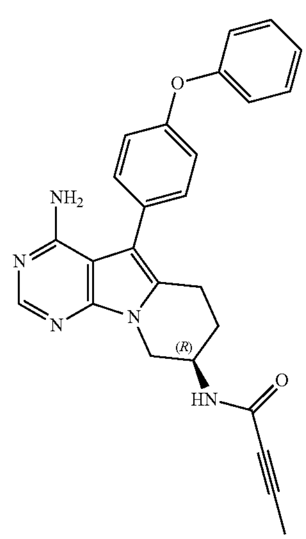 |
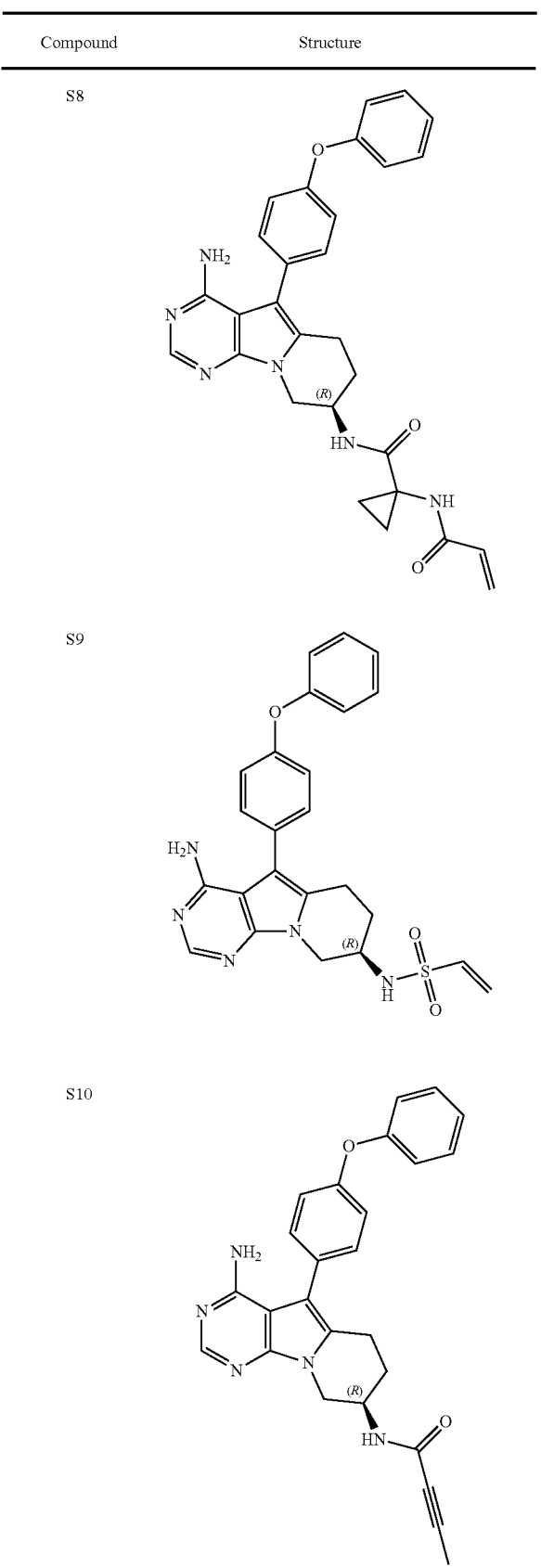
-continued
| Compound | Structure |
|---|---|
| S11 | 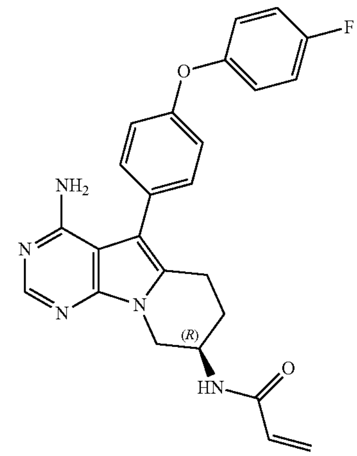 |
| S12 | 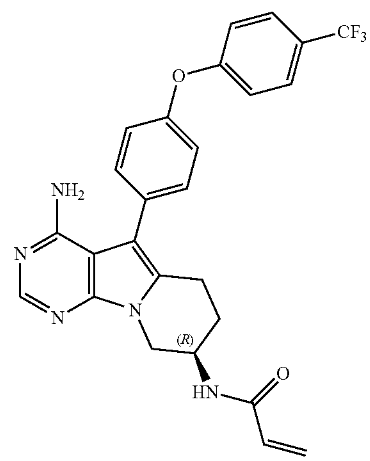 |
| S13 | 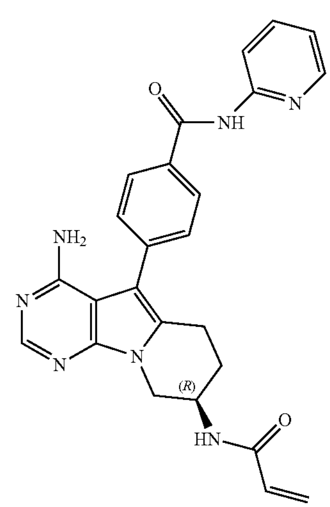 |
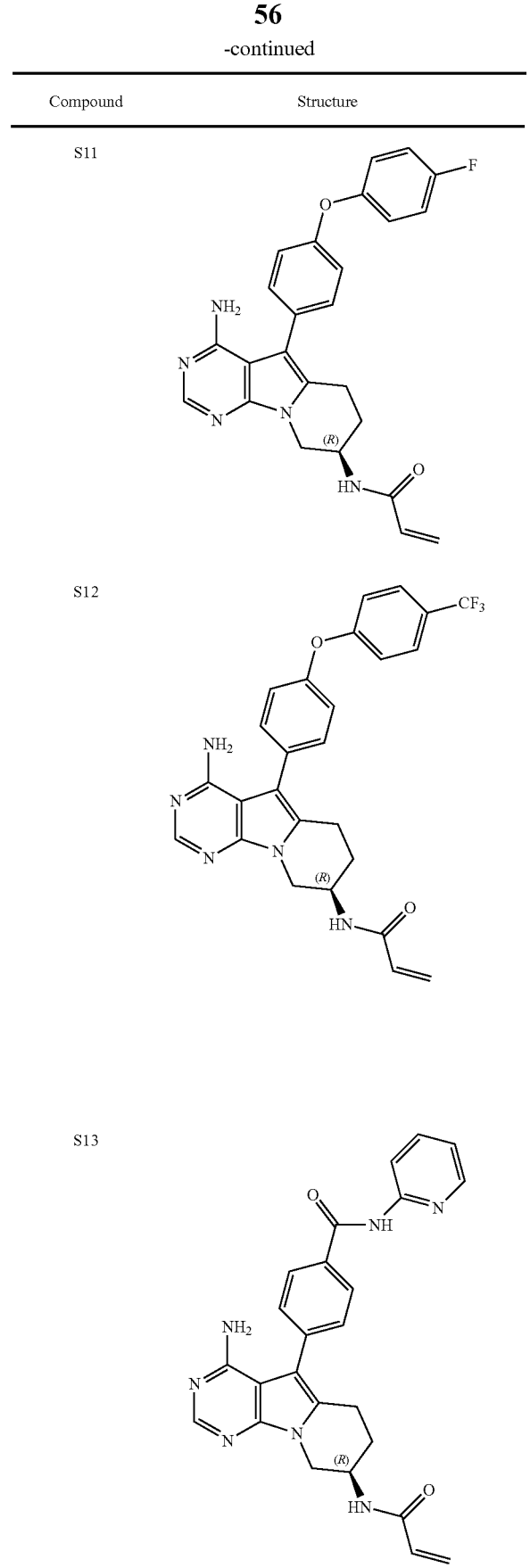

-continued
| Compound | Structure |
|---|---|
| S14 | 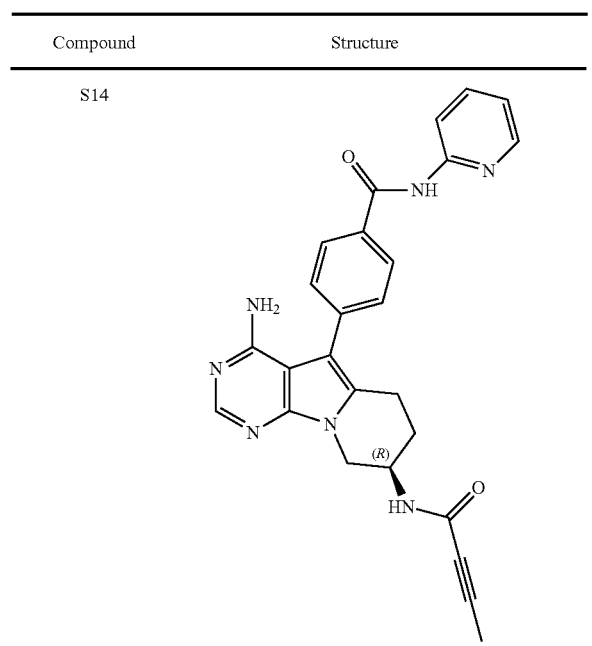 |
| S15 | 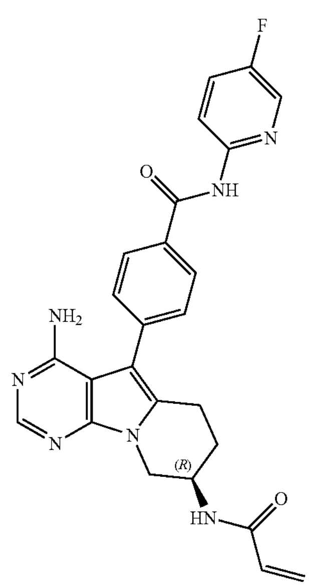 |
-continued
| Compound | Structure |
|---|---|
| S16 | 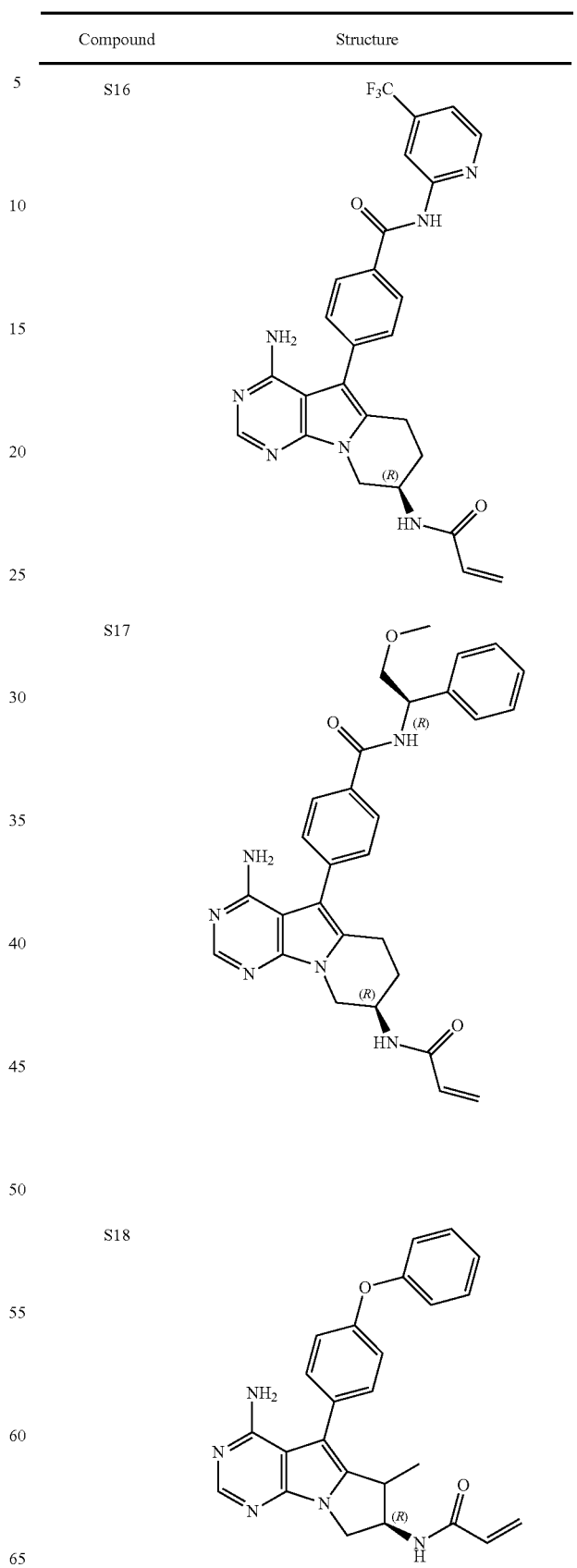 |
| S17 | 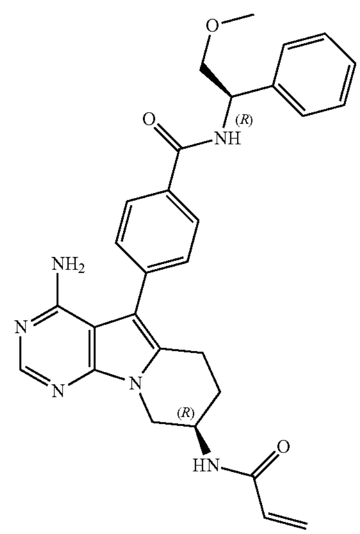 |
| S18 | 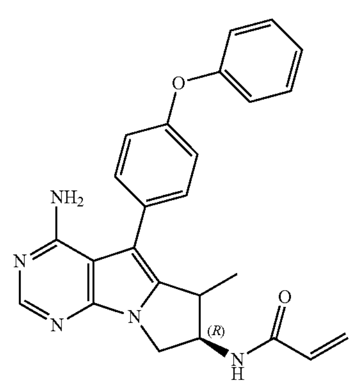 |

| Compound | Structure |
|---|---|
| S19 | 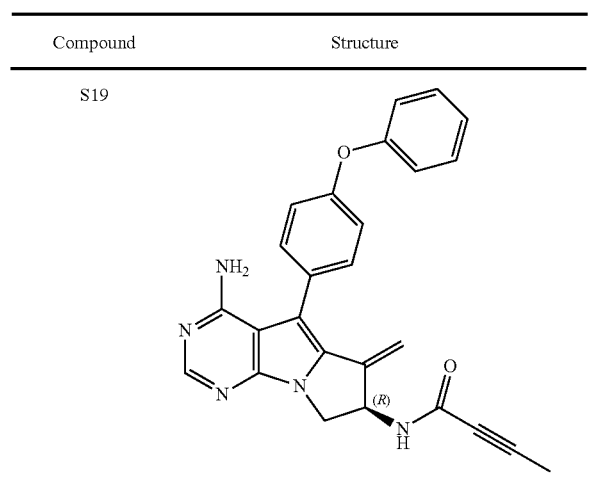 |
| S20 | |
| Compound | Structure |
|---|---|
| S21 | 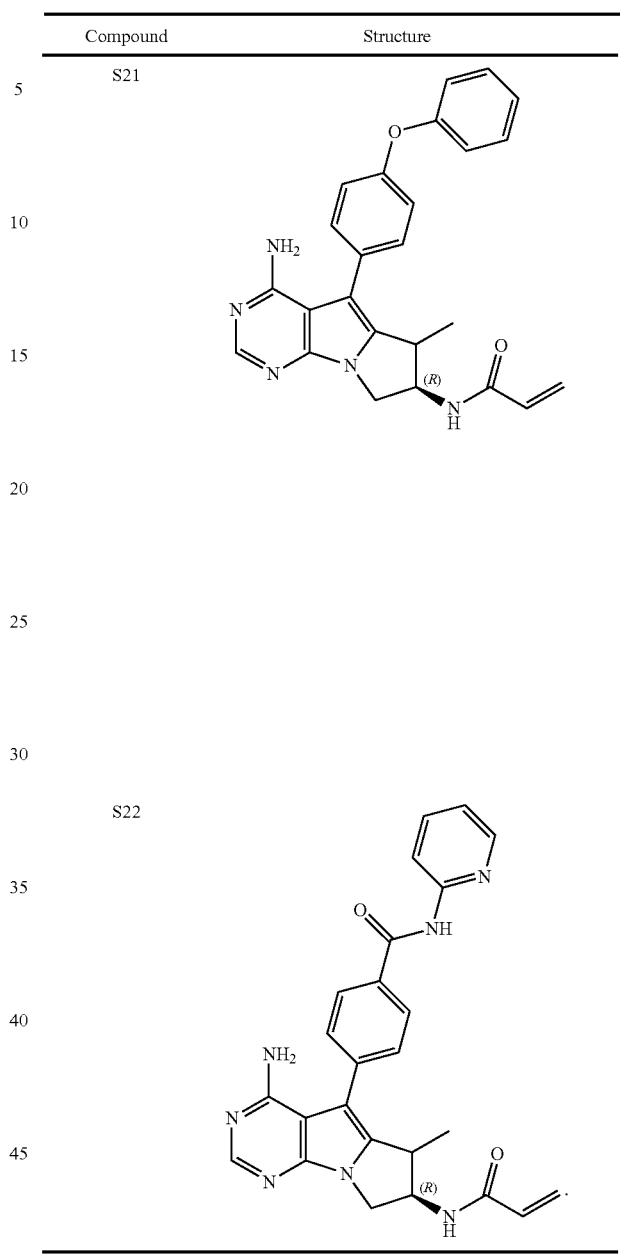 |
| S22 | |
6. A method for preparing a 5-aryl-pyrimidoindolizine or 5-aryl-pyrimidopyrrolizine compound, the preparation method comprising:
Scheme 1
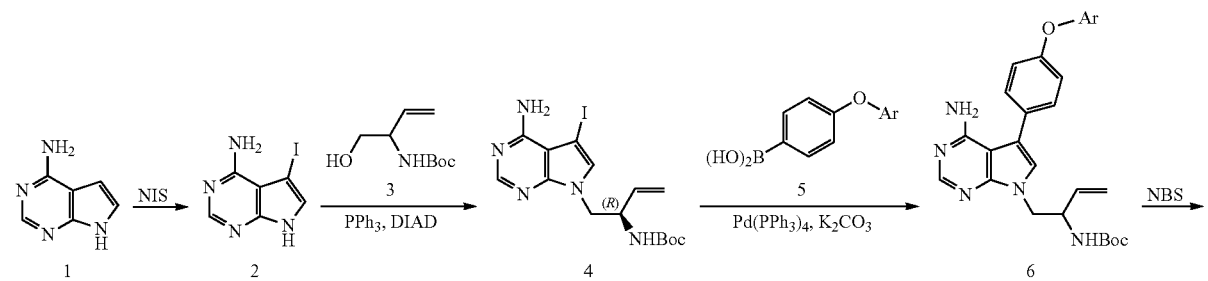

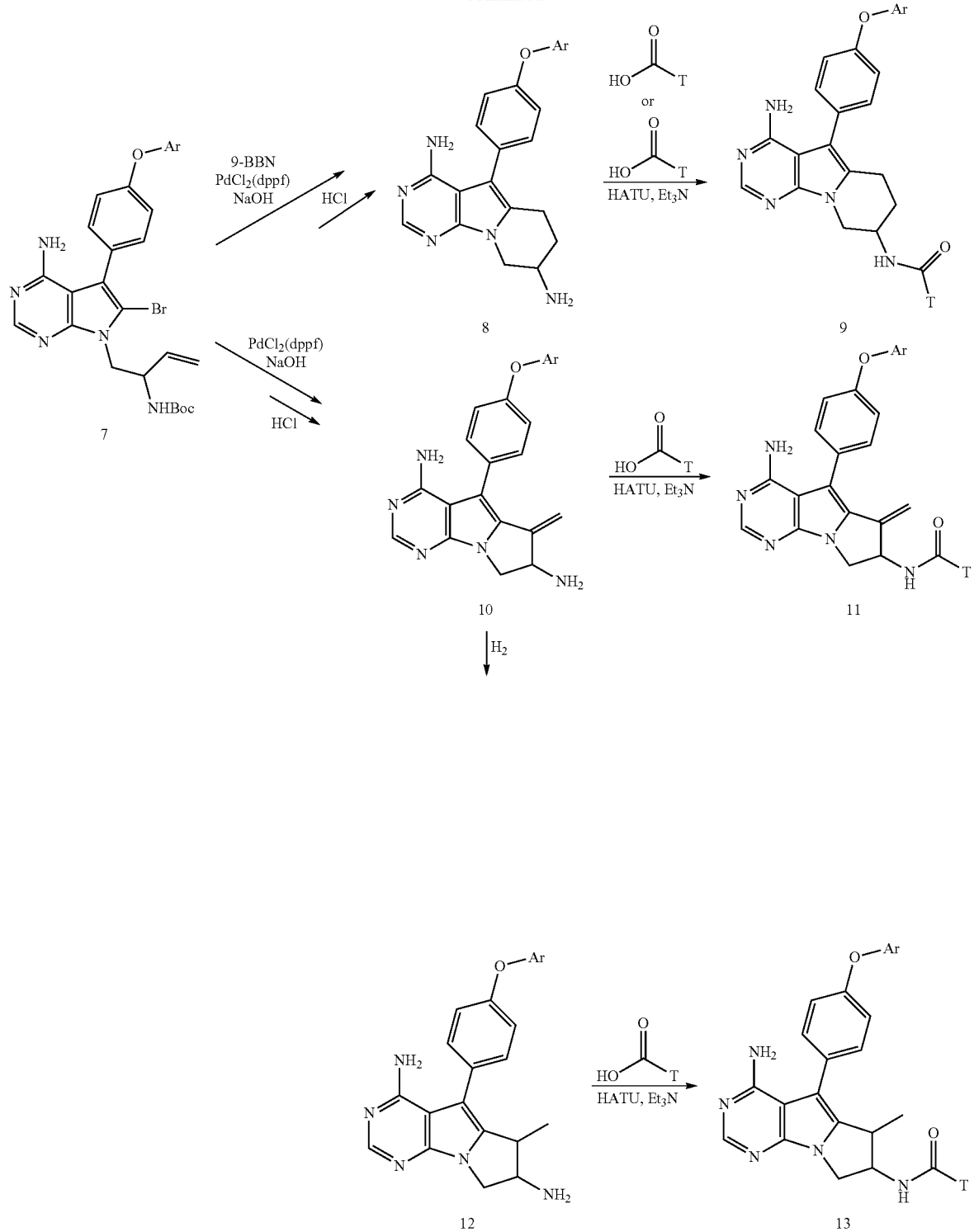

Scheme 1a:
4-amino-pyrrolo[2,3-d]pyrimidine, i.e. Compound 1 as a starting material is iodo-substituted with N-iodosuccinimide (NIS) on 5-position to give Compound 2, Fragment 3 is incorporated into Compound 2 through Mitsunobu reaction to give compound 4, Compound 4 is coupled with a substituted phenylboronic acid or borate to give Compound 6, Bromine is introduced at 6-position of Compound 6 by N-bromosuccinimide (NBS) to give Compound 7, Compound 7 reacts with 9-boronbicyclo[3.3.1]nonane (9-BBN) in anhydrous tetrahydrofuran (THF), then forms a six-membered ring through a self-Suzuki- Miyaura coupling in the presence of [1,1-bis(diphenyl-phosphinyl)ferrocene]palladium dichloride (PdCl$_2$(dppf)), and is deprotected to give Compound 8 with a core of tetrahydrogenpyrido[5,4-b]indole, Compound 8 condensates with a carboxylic acid or a sulfonic acid to give Compound 9, or Scheme 1b:

Compound 7 forms a five-membered cyclic compound through an intramolecular Heck reaction in the presence of PdCl$_2$(dppf), and is deprotected to give Compound 10, which condensates with a substituted carboxylic acid to give Compound 11, or Scheme 1c:

Compound 10 is hydrogenated in the presence of a catalyst to give Compound 12,

Compound 12 condensates with an acid to give Compound 13;

or

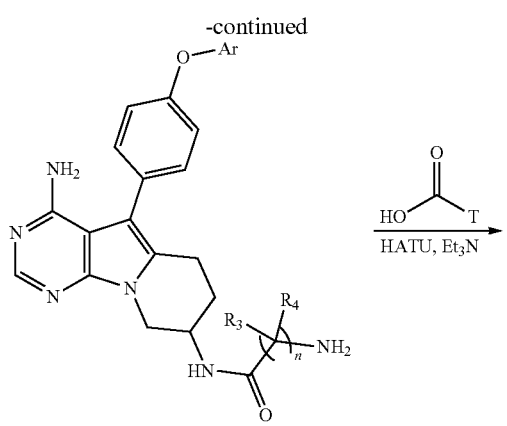

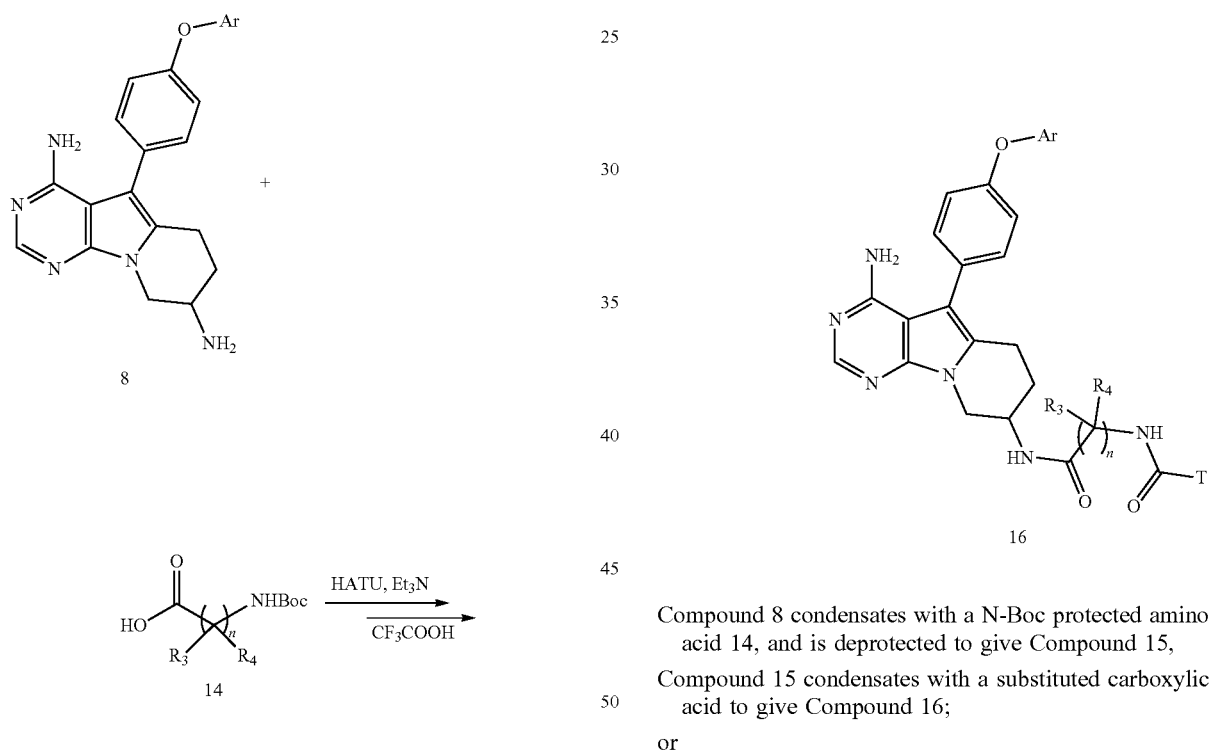

Compound 8 condensates with a N-Boc protected amino acid 14, and is deprotected to give Compound 15, Compound 15 condensates with a substituted carboxylic acid to give Compound 16;

or

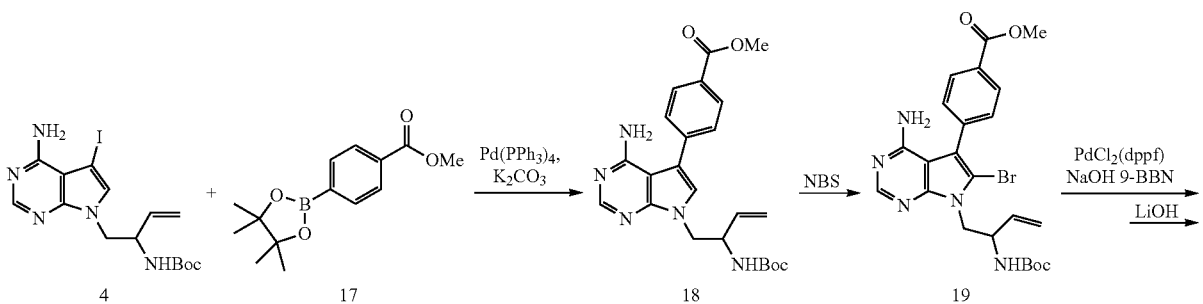

-continued

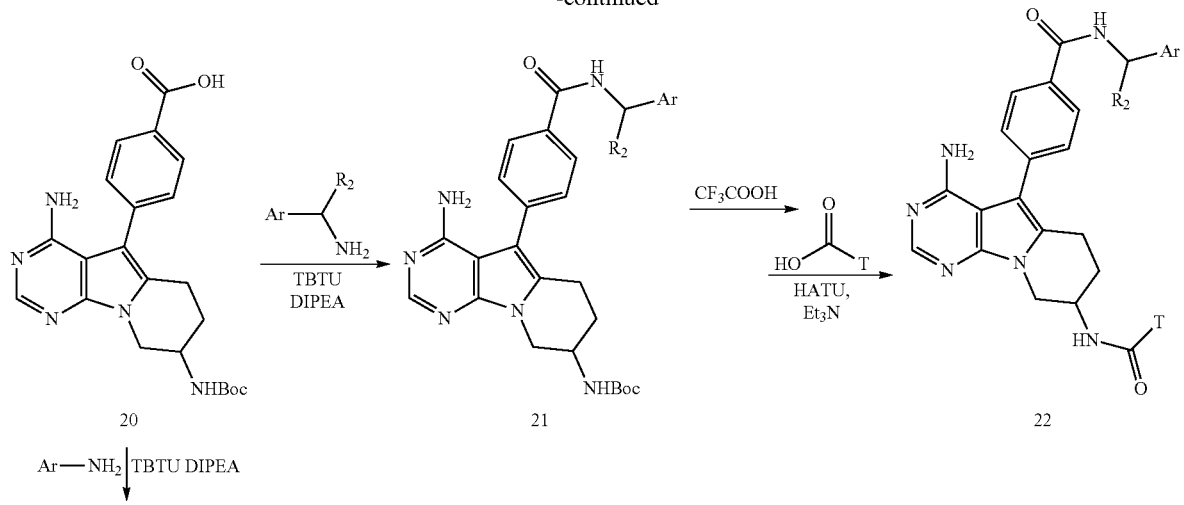

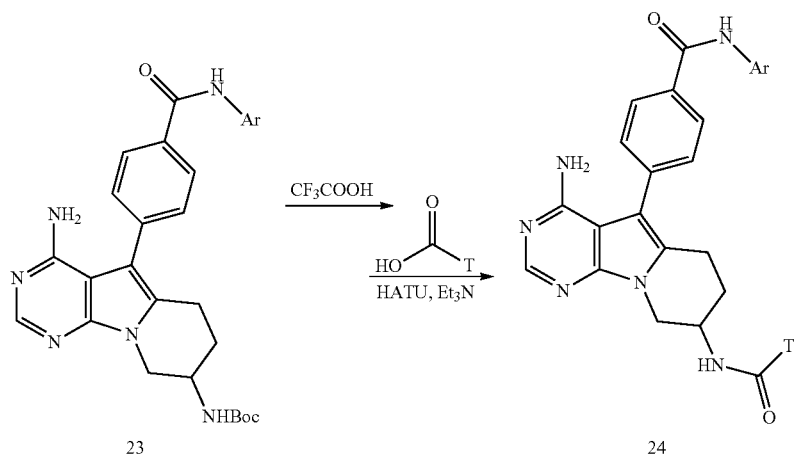

Scheme 3a:
Compound 4 is coupled with a substituted phenylboronic acid or borate 17 to give Compound 18,
Bromine is incorporated at 6-position of Compound 18 by NBS to give brominated Compound 19,
Compound 19 reacts with 9-BBN in anhydrous THF, forms a six-membered ring through a self-Suzuki-Miyaura coupling in the presence of PdCl$_2$(dppf), and then is hydrolyzed in the presence of lithium hydroxide to give Compound 20,
Compound 20 condensates with a substituted alkylamine to give Compound 21,
Compound 21 is deprotected and condensates with a carboxylic acid to give Compound 22, or
Scheme 3b:
Compound 20 condensates with an arylamine to give Compound 23,
Compound 23 is deprotected and condensates with a carboxylic acid to give Compound 24;
or Scheme 4

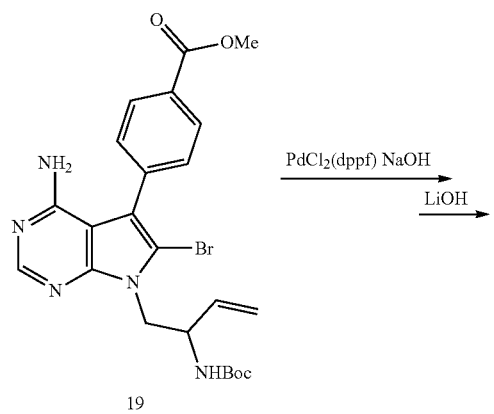

Brominated compound 19 forms a five-membered cyclic compound through an intramolecular Heck reaction in the presence of PdCl₂(dppf), and treated with LiOH to give a carboxylic acid 25, The carboxylic acid 25 condensates with an arylamine to give an amide 26, The amide 26 is hydrogenated in the presence of a catalyst to give Compound 27, Compound 27 is deprotected with CF₃COOH to remove Boc-protection, and condensates with a carboxylic acid to give Compound 28, in the above schemes, $R_2$ is hydrogen or substituted or unsubstituted C1-C3 alkyl, wherein the substituent in $R_2$ is halogen or C1-C3 alkoxy;

Ar is substituted or unsubstituted C6-C20 aryl, substituted or unsubstituted 5-20 membered heteroaryl containing one or more heteroatoms selected from the group consisting of O, N and S, wherein the substituent in Ar is halogen, C1-C6 alkyl, C1-C6 alkoxy, trifluoromethyl or trifluoromethoxy;

$R_3$ and $R_4$ may be independently hydrogen or C1-C3 alkyl, or $R_3$, $R_4$ and the carbon atom attached thereto form C3-C5 cycloalkyl;

n is 0, 1 or 2;

T is

[structure showing $R_5$, $R_6$, $R_7$ alkene or alkyne with $R_8$]

or ≡—$R_8$;

$R_5$, $R_6$ and $R_7$ may be independently selected from the group consisting of hydrogen, cyano, halogen, and substituted or unsubstituted C1-C20 alkyl, preferably are independently selected from the group consisting of hydrogen, cyano, halogen, and substituted or unsubstituted C1-C10 alkyl, more preferably are independently selected from the group consisting of hydrogen, cyano, halogen, and substituted or unsubstituted C1-C5 alkyl; the substituent in $R_5$, $R_6$ or $R_7$ is dimethylamino, C1-C10 alkoxy, or 3 to 10 membered heterocyclyl containing one or more heteroatoms selected from the group consisting of O, N and S; preferably dimethylamino, C1-C6 alkoxy, or 3 to 10 membered heterocyclyl containing one or more heteroatoms selected from the group consisting of O, N and S; more preferably dimethylamino, C1-C5 alkoxy, or 3 to 6 membered heterocyclyl containing 1 to 3 heteroatoms selected from the group consisting of O, N and S;

$R_8$ is selected from the group consisting of hydrogen and C1-C10 alkyl, preferably selected from the group consisting of hydrogen and C1-C5 alkyl, more preferably selected from the group consisting of hydrogen and C1-C3 alkyl.

7. A pharmaceutical composition comprising a therapeutically effective amount of the 5-aryl-pyrimidoindolizine or 5-aryl-pyrimidopyrrolizine compound or a pharmaceutically acceptable salt thereof according to claim 1, and one or more pharmaceutically acceptable carriers.

8. A method of treating lymphoma comprising administrating the 5-aryl-pyrimidoindolizine or 5-aryl-pyrimidopyrrolizine compound or a pharmaceutically acceptable salt thereof according to claim 1 to a subject in need thereof.

* * * * *